United States Patent
Sadamasa

[19]

[11] Patent Number: 6,017,339
[45] Date of Patent: Jan. 25, 2000

[54] ENDOSCOPIC DIATHERMIC KNIFE

[75] Inventor: Akihito Sadamasa, Hachioji, Japan

[73] Assignee: Olympus Optical Co., Ltd., Tokyo, Japan

[21] Appl. No.: 08/787,340

[22] Filed: Jan. 27, 1997

[30] Foreign Application Priority Data

Feb. 5, 1996 [JP] Japan ................................ 8-018926

[51] Int. Cl.$^7$ .................................................. A61B 17/36
[52] U.S. Cl. ............................................. 606/46; 606/47
[58] Field of Search ................................. 606/42, 45, 46,
606/47; 600/373, 374, 144, 146, 149; 607/122,
119; 604/282

[56] References Cited

U.S. PATENT DOCUMENTS

| | | | |
|---|---|---|---|
| 5,024,617 | 6/1991 | Karpiel | 606/47 |
| 5,323,768 | 6/1994 | Saito et al. | 606/47 |
| 5,487,757 | 1/1996 | Truckai et al. | 607/122 |
| 5,715,817 | 2/1998 | Stevens-Wright et al. | 607/122 |

FOREIGN PATENT DOCUMENTS

| | | |
|---|---|---|
| 33 47 122 | 6/1985 | Germany . |
| 35 43 594 | 7/1986 | Germany . |
| 57597 | 1/1993 | Japan . |
| 568685A | 3/1993 | Japan . |
| 653125 B2 | 7/1994 | Japan . |

*Primary Examiner*—Linda C. M. Dvorak
*Assistant Examiner*—David Ruddy
*Attorney, Agent, or Firm*—Kenyon & Kenyon

[57] ABSTRACT

The knife has the flexible, electrically insulating casing (24) inserted into a body cavity via an endoscope. A wire within this casing receives the HF current from a HF source and can be displaced to project relative to a suction opening (38) at the distal end of the casing to define the cutting zone (42).

The operating device at the proximal end of the casing has a suction mouthpiece coupling to the suction opening (38). The casing is strengthened via an inserted support ring (56) between the suction opening (38) and the cutting zone (42) and/or via an internal strengthening wire (50).

ADVANTAGE—Prevents blockage of suction path during bending. (20 pp Dwg.No. 6/13)

18 Claims, 16 Drawing Sheets

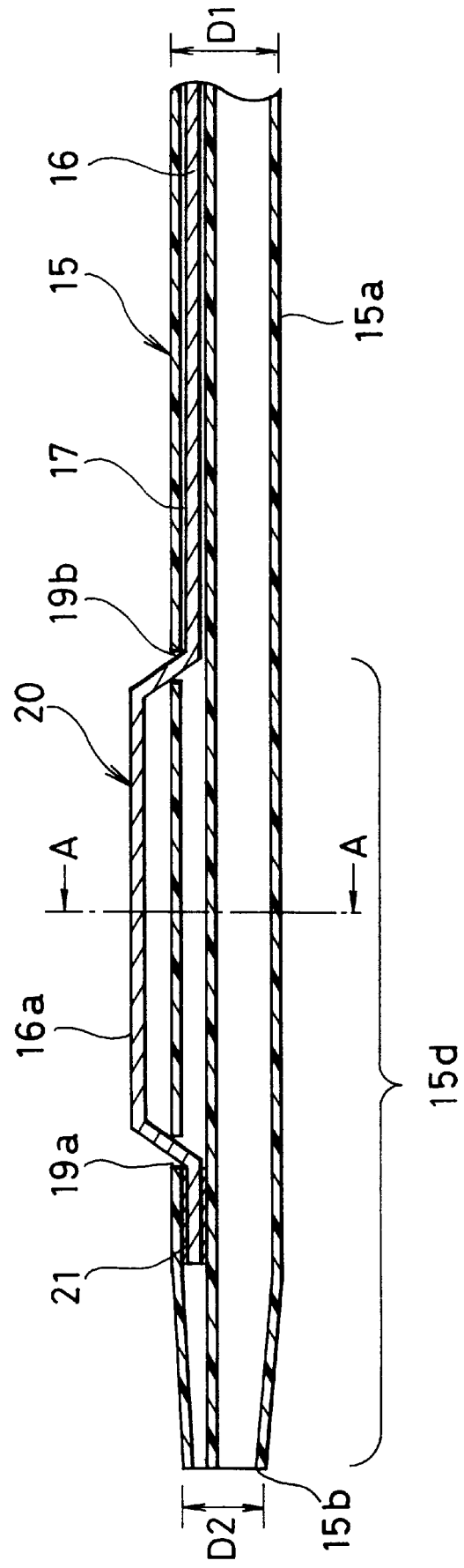

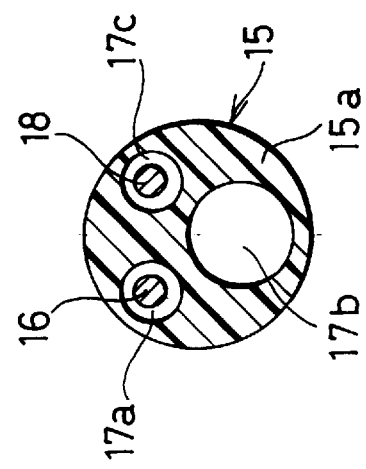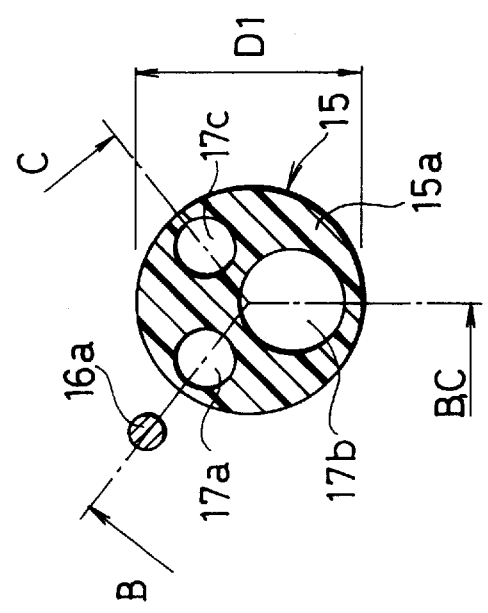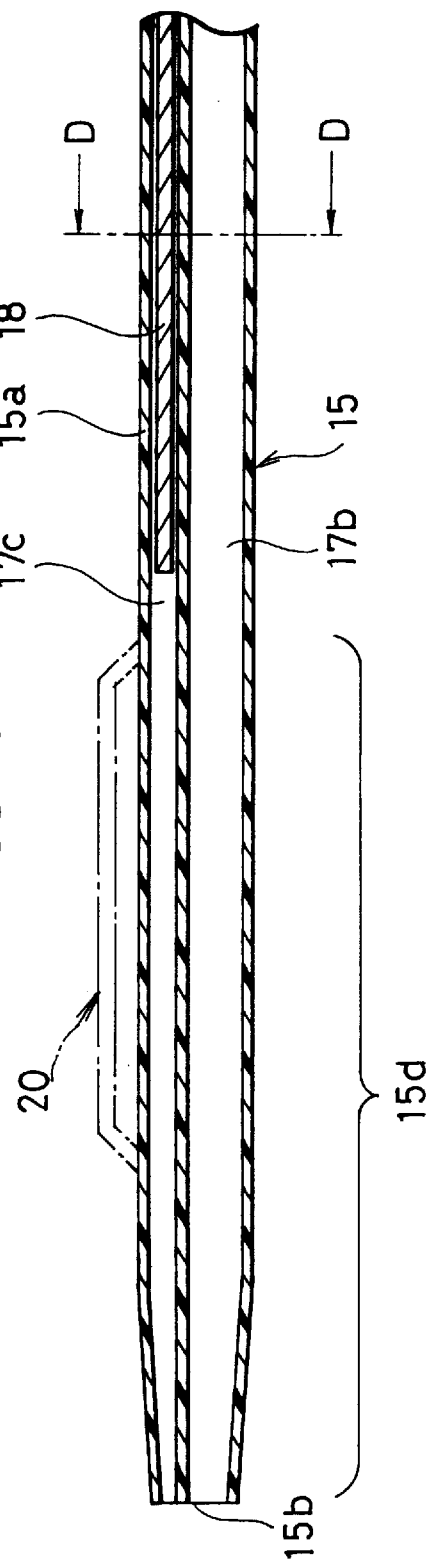

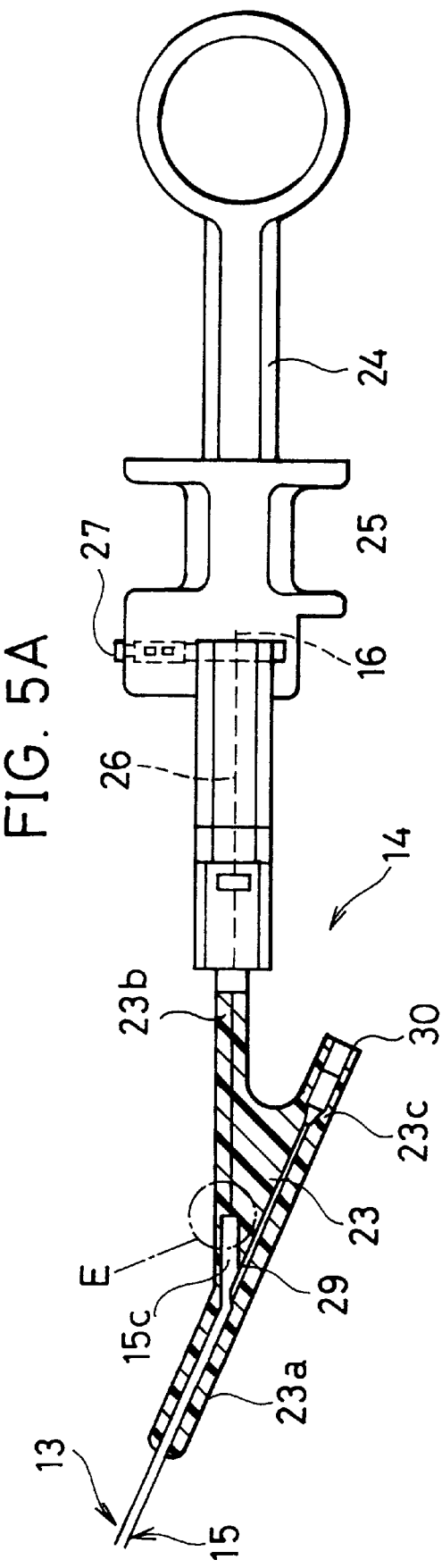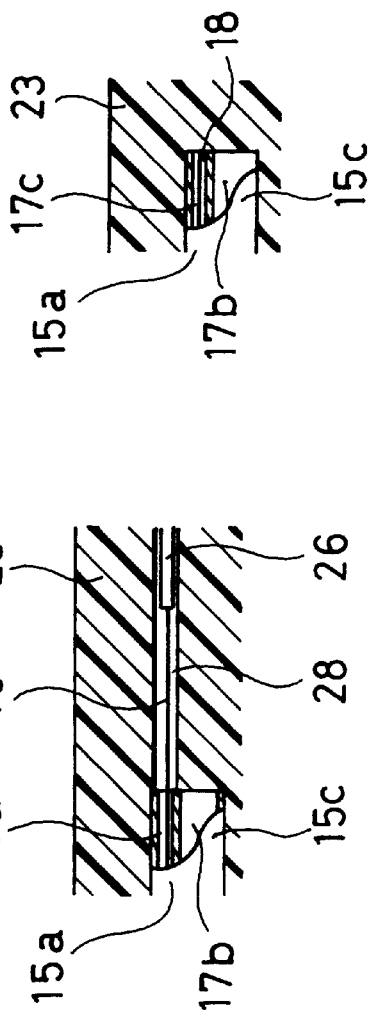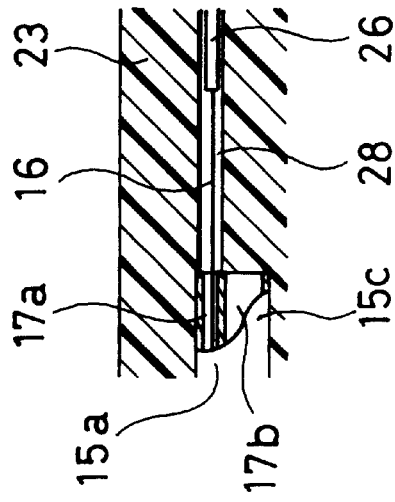

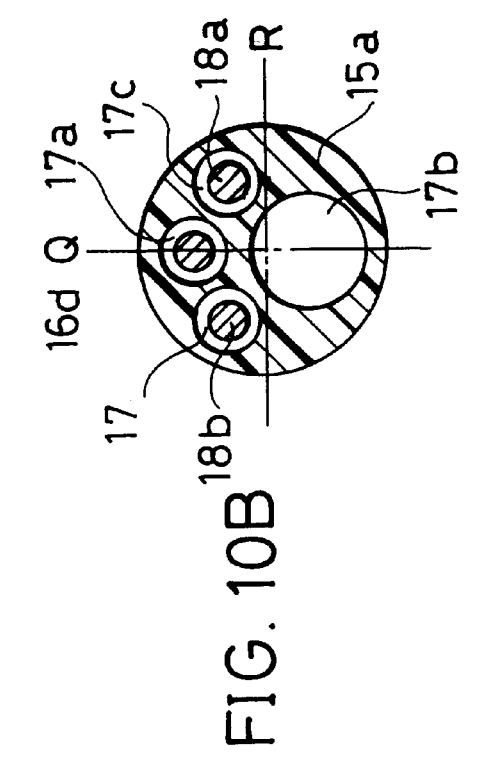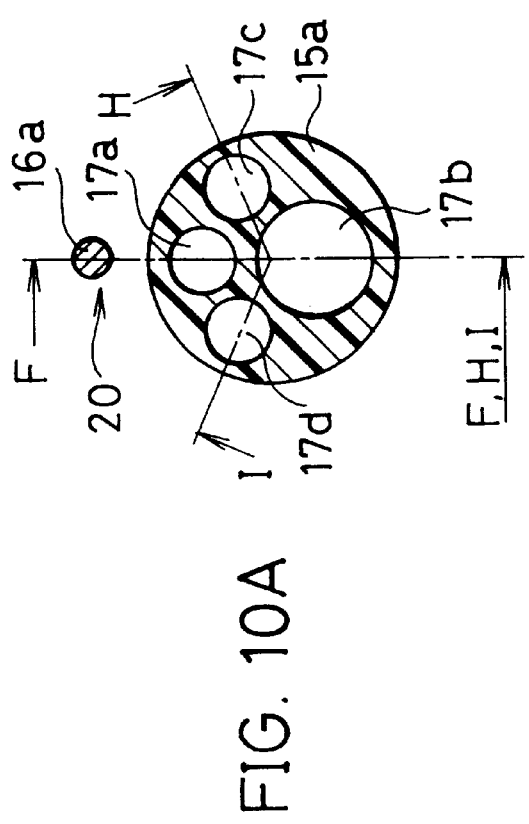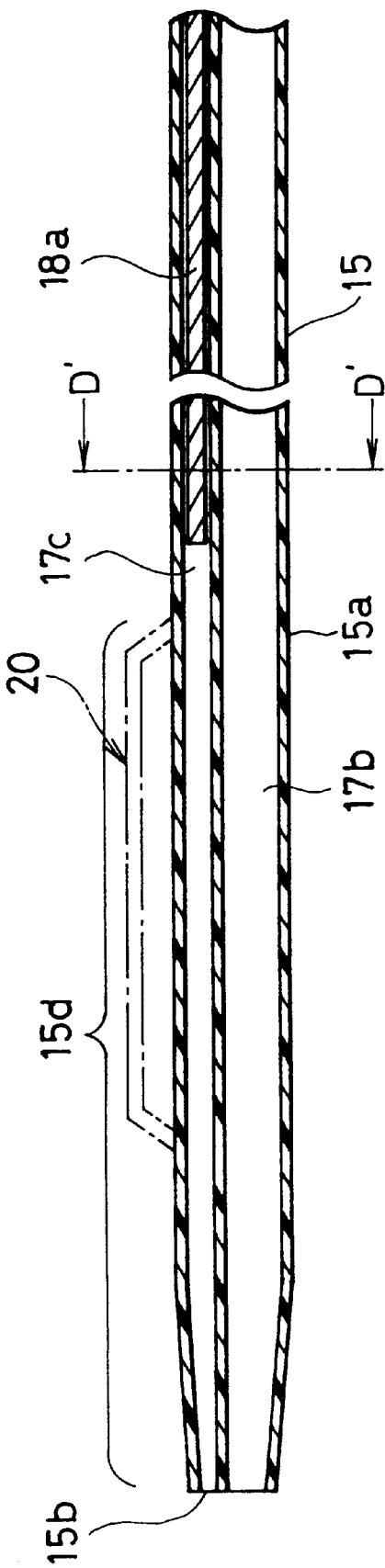

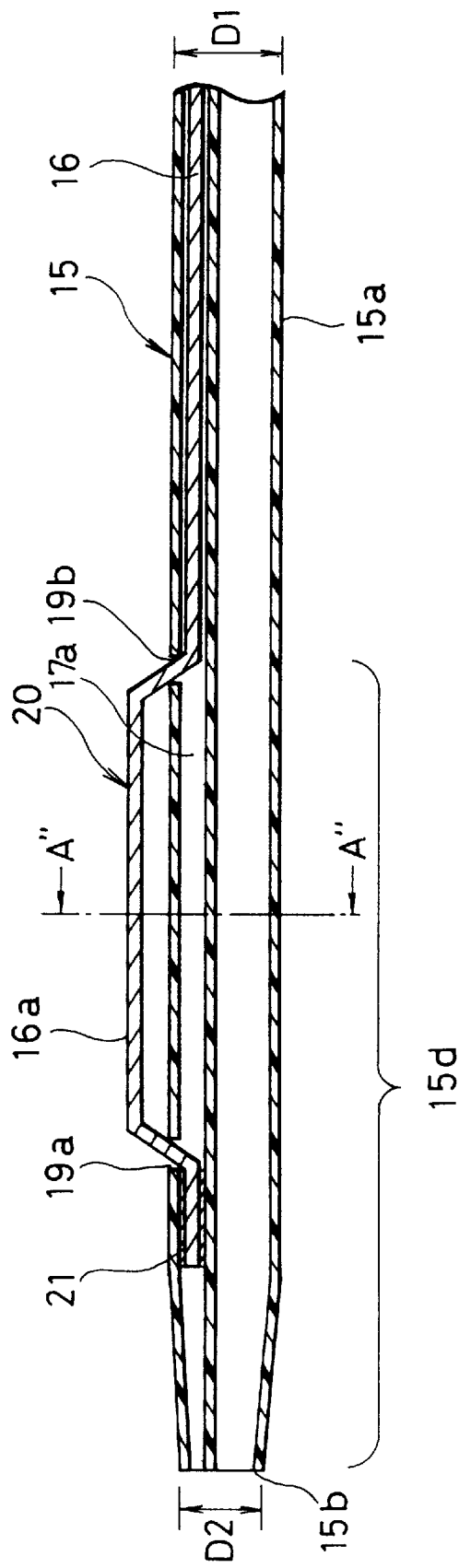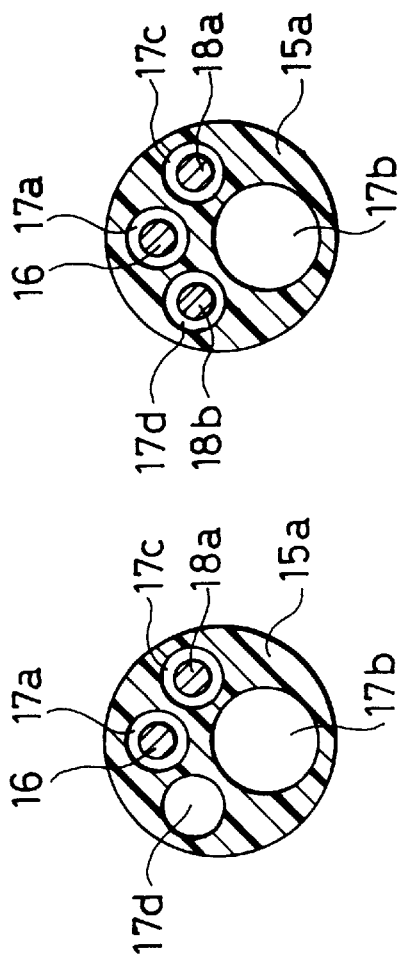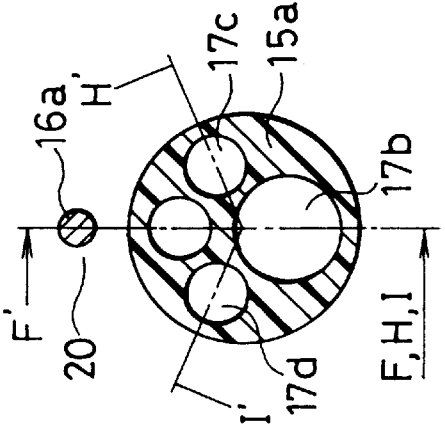

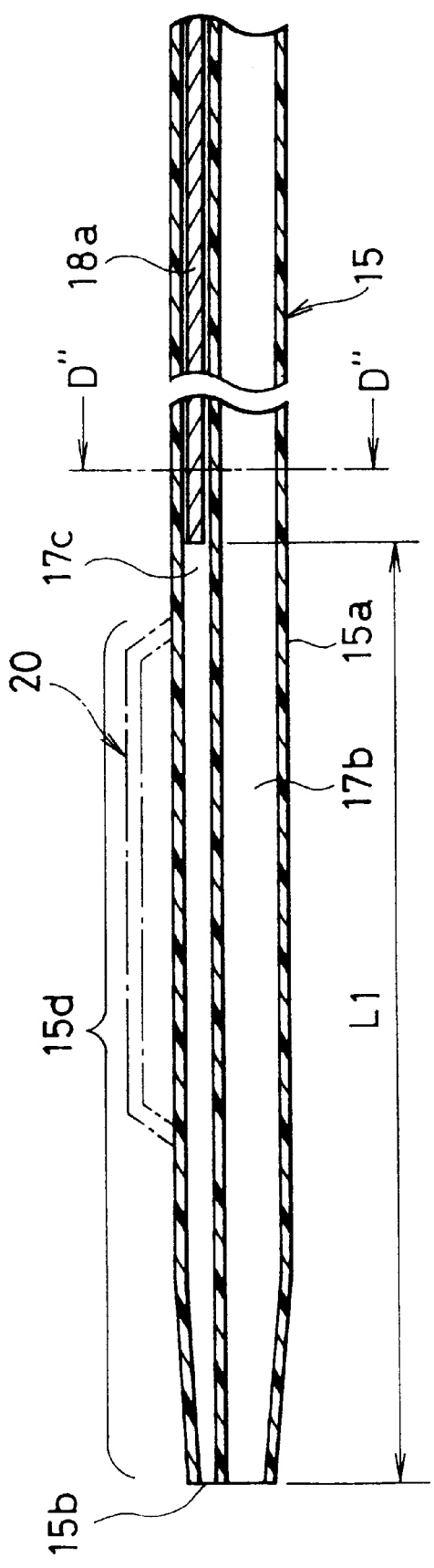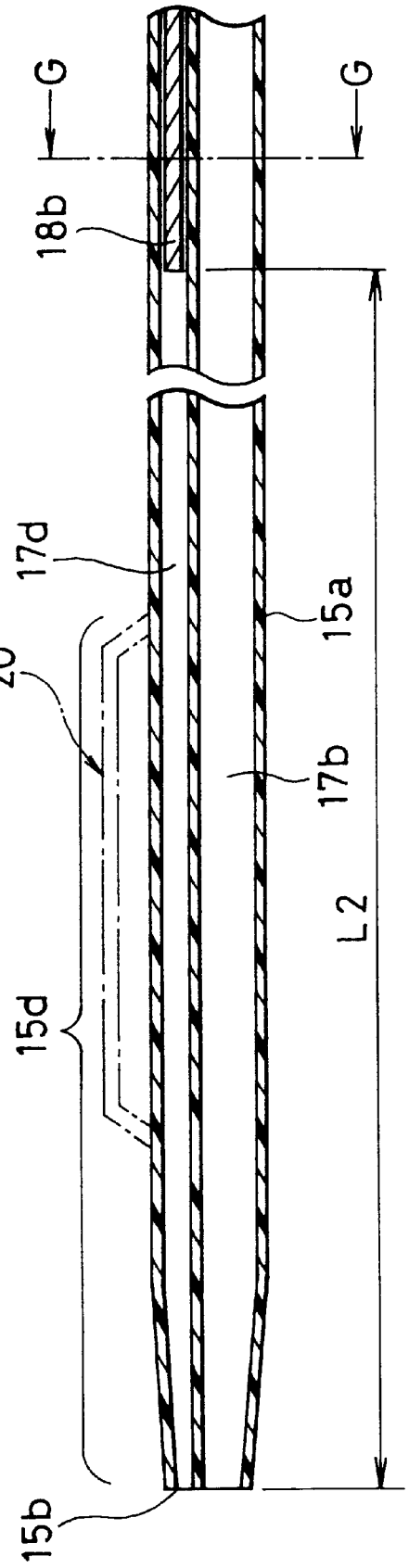

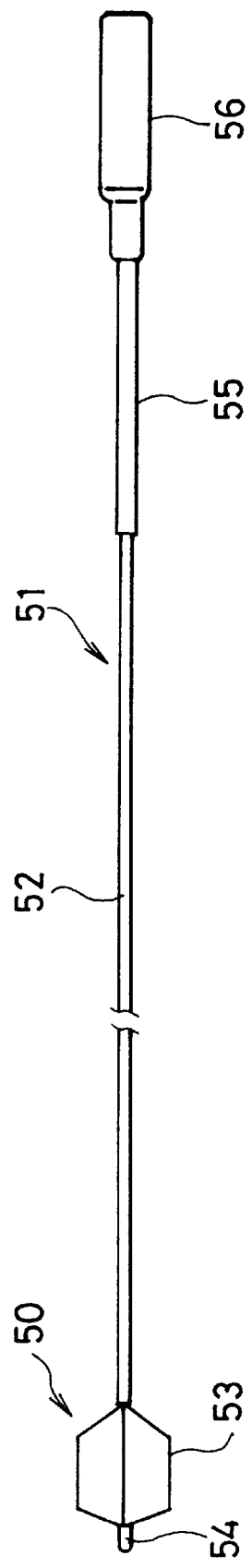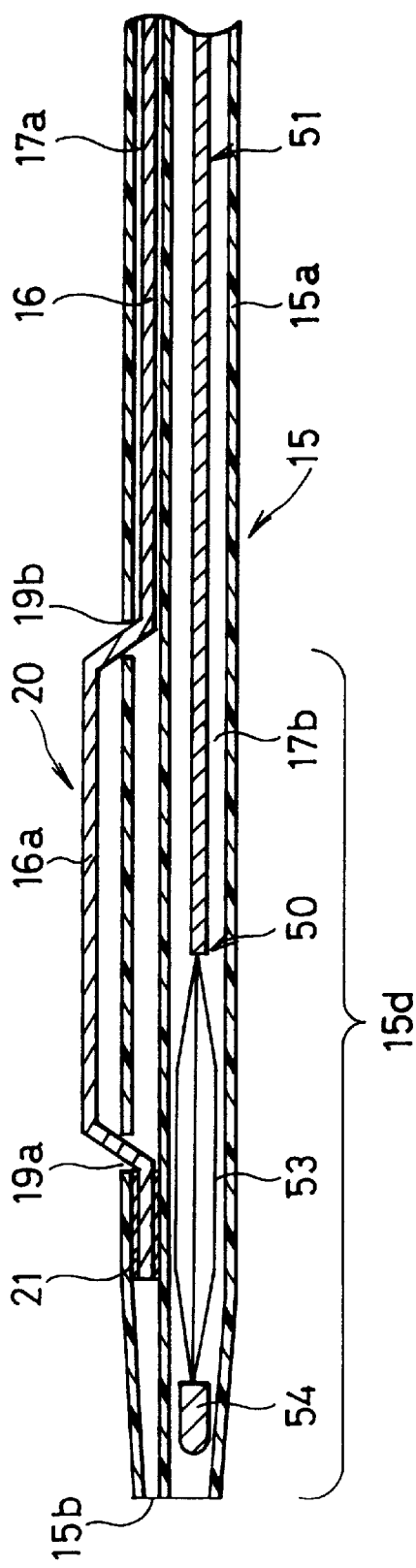

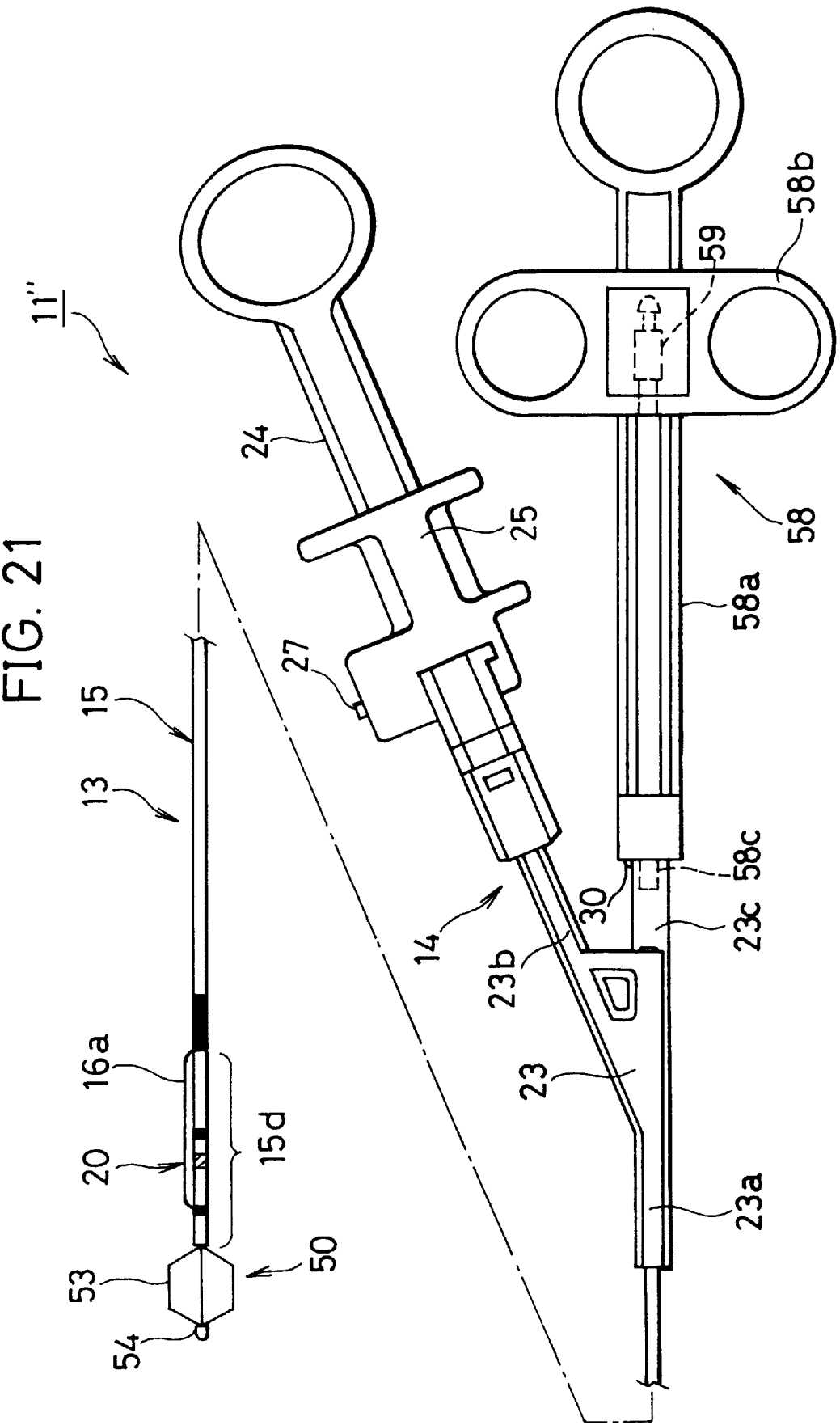

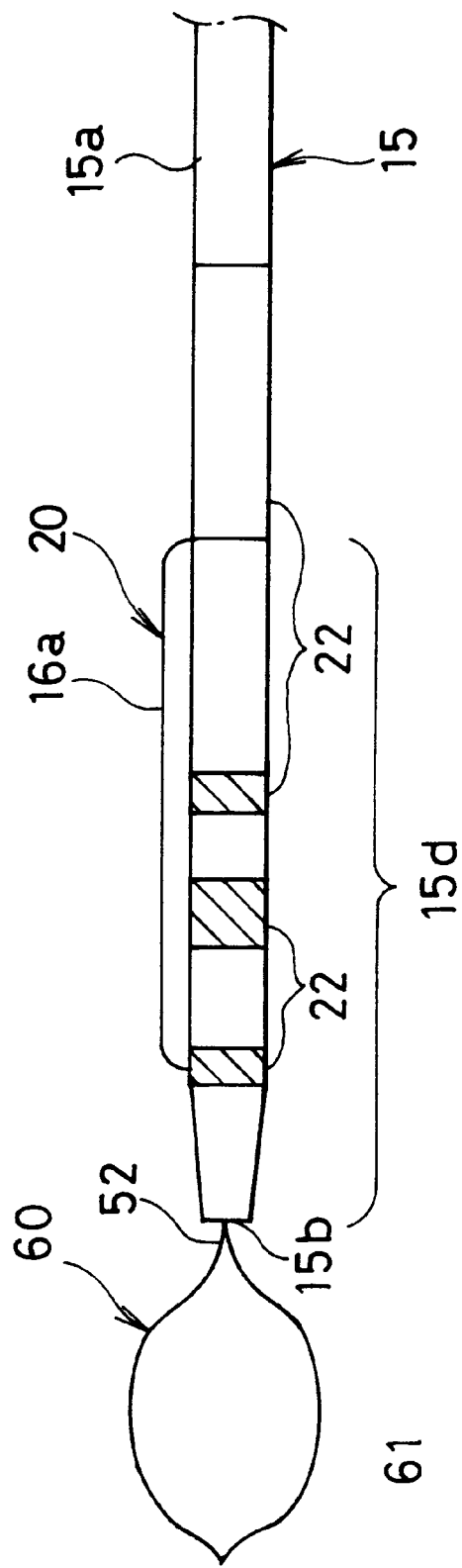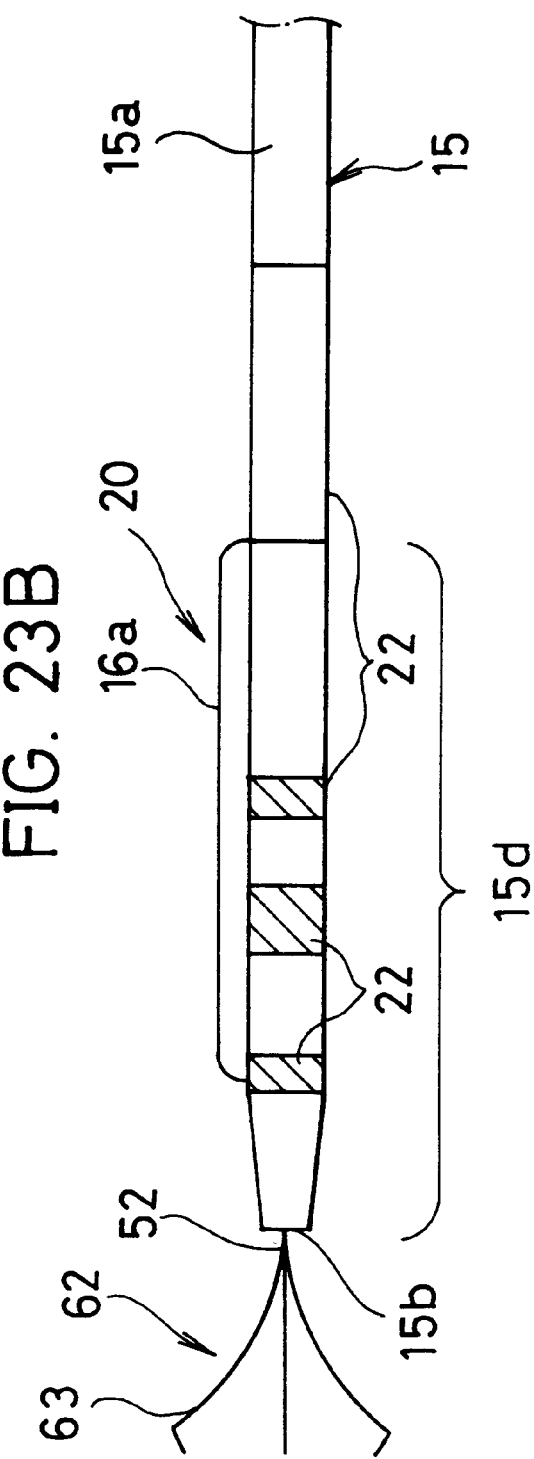

ENDOSCOPIC DIATHERMIC KNIFE

BACKGROUND OF THE INVENTION

1. Field of the Invention

The present invention relates to an endoscopic diathermic knife for performing endoscopic sphincterotomy (EST) or endoscopic papillotomy (EPT).

2. Description of the Related Art

Japanese laid-open patent publications 5-7597 and 5-68685 each disclose a diathermic knife, in which a knife portion is formed by exposing an electrically conductive wire introduced into a lumen of a tube to the outside of an external wall surface of a distal end portion of the tube. The distal end portion of the tube is bent in a bow-like shape by pulling the conductive wire by an operation on its proximal end side, and the knife portion is pushed on a part to be treated to cut it by a high frequency current. Such a diathermic knife employs a relatively soft tube so that the distal end portion of the tube can be easily bent.

Furthermore, Japanese examined patent publication 6-53125 discloses an instrument which is provided with a reinforcing means of a rectangular cross section in the range from the distal end portion to the proximal end portion within a lumen of a tube in order to control the direction of cutting a sphincter.

In the diathermic knives disclosed in Japanese laid-open patent publications 5-7597 and 5-68685, when the conductive wire is pulled by the operation on the proximal end side to bend the distal end portion of the tube in the bow-like shape, the tube is somewhat easy to bend because it is soft. However, since the tube flexes over its full length, there has been the operational problem that the distal end portion of the tube can not be easily bent due to frictional resistance between the conductive wire and the lumen of the tube.

Further, there has been the problem that, when such a diathermic knife is pushed into a treating instrument inserting channel of an endoscope and a narrow cavity in a living body, the tube also flexes in its axial direction and the pushing operation on the proximal end side is not effectively transmitted to the distal end portion so that its insertion is not easy.

When the endoscopic sphincterotomy is performed by using such an endoscopic diathermic knife, the knife is used usually with an endoscope of a side view type having a bending mechanism and a treating instrument upheaving device.

First, the endoscope is inserted into a duodenum and bent by a bending operation thereof to observe a duodenal papilla directly. Next, the endoscopic diathermic knife is introduced through a treating instrument inserting channel of the endoscope and inserted into a bile duct through the papilla by the operation of the treating instrument upheaving device and the bending operation. Then, the conductive wire is pulled by the operation on the proximal end side of the endoscopic diathermic knife to bend the distal end portion of the tube in a bow-like shape, and the knife portion is pushed on a duodenal papillary sphincter to cut it by a high frequency current.

FIG. 6 shows how the endoscopic sphincterotomy is performed, and FIG. 8 shows an endoscopic image of the state shown in FIG. 6

As shown in FIG. 6, in order to observe the papilla directly, it is necessary from an anatomical point of view to bend the bending portion of the endoscope so that the center of curvature is on the side of the field of view of the endoscope. Moreover, in order to bring the endoscopic diathermic knife to the field of view of the endoscope and easily insert the distal end into the bile duct, it is necessary to upheave the endoscopic diathermic knife toward the field of view of the endoscope by operating the treating instrument upheaving device.

Furthermore, as shown in FIG. 8, in order to perform the endoscopic sphincterotomy safely without causing complications, it is necessary to cut upward in the plane of the paper, that is, the so-called twelve o'clock direction within the field of view of the endoscope.

Accordingly, as shown in FIG. 6, when performing the endoscopic sphincterotomy, the bending direction of the endoscope, the direction of upheaving the endoscopic diathermic instrument by the treating instrument upheaving device, and the knife portion in the distal end portion of the tube are positioned substantially in the same plane, and the distal end portion of the tube has a bending shape with the knife portion directed inwardly.

In imitation of the aforesaid bending shape of the tube, doctors give a bending tendency to the distal end portion of the tube beforehand so as to direct the knife portion inward, so that the knife portion is directed to the twelve o'clock direction in the field of view of the endoscope when the endoscopic diathermic knife goes out of the distal end portion of the endoscope. That is, the bending tendency of the tube is fitted to the bending shape of the endoscope and the direction of the treating instrument upheaving device to stabilize the direction of the knife portion.

However, the doctors cannot always give the bending tendency stably to the distal end portion of the tube. Accordingly, there has been the problem that the direction of the knife portion with respect to the endoscope is not stable.

If the reinforcing means provided in the lumen of the tube of the instrument as disclosed in Japanese examined patent publication 6-53125 is applied to the endoscopic diathermic knives as disclosed in Japanese laid-open patent publications 5-7597 and 5-68685, the problems of operation and insertion caused by the flexing of the entire tube of the aforesaid endoscopic diathermic knife will be somewhat solved because the full length of the tube is reinforced.

Moreover, by virtue of the regulation of the bending direction of the tube by the reinforcing member of the instrument in Japanese examined patent publication 6-53125, the bending direction of the tube coincides with the bending shape of the endoscope and the direction of the treating instrument upheaving device, so that the problem of the direction of the knife portion will be solved.

However, in the instrument of Japanese examined patent publication 6-53125, because the reinforcing member is provided also in the lumen of the knife portion in the distal end portion of the tube, the reinforcing member becomes resistant to the bending when the distal end portion of the tube is bent in a bow-like shape. Consequently, the problem of not being able to easily handle the distal end portion of the tube is not solved.

Moreover, because the distal end portion of the tube is rigid, when inserting the distal end portion of the tube into the bile duct through the papilla, a part near the papilla and the inside wall of the bile duct will be injured, and danger of causing other complications such as perforation and bleeding is high, thereby raising a problem of safety.

SUMMARY OF THE INVENTION

An object of the present invention is to solve the problems in the conventional art and provide an endoscopic diathermic knife which is easy to operate and insert into a channel or a living body and which is safe from injuring the living body.

Another object of the present invention is to provide an endoscopic diathermic knife which is easy to manipulate.

Therefore, an endoscopic diathermic knife according to the present invention comprises a reinforcing member provided in the range from the vicinity of a proximal end portion of a sheath body to the vicinity of a wire lead-out opening.

With this structure, the sheath becomes rigid so that the sheath can be prevented from flexing during its operation to secure a good operability. Further, when the sheath is inserted and pushed into a narrow cavity or an endoscopic channel, the sheath does not excessively flex so that good insertion can be attained. Moreover, since the knife portion of the sheath is soft, the distal end portion of the sheath can be easily bent to secure a better operability. Furthermore, because the distal end portion of the sheath is also soft, it does not injure the living body so that this endoscopic diathermic knife can be used safely.

Another object of the present invention is to provide an endoscopic diathermic knife, in which its knife portion has a stable directional relationship to an endoscope.

Therefore, an endoscopic diathermic knife according to the present invention comprises a reinforcing member provided in the range from the vicinity of a proximal end portion of a sheath body to the vicinity of a wire lead-out opening, and the reinforcing member is arranged eccentric to the central axis of the sheath.

With this structure, in addition to the above-mentioned good operability, insertion, and safety, the stable directional relationship of the knife portion with the endoscope can be realized, because the bending direction of the sheath near the proximal end of the knife portion is regulated by the reinforcing member.

Other characteristics and advantages of the present invention will be apparent from the following description.

BRIEF DESCRIPTION OF THE DRAWINGS

FIGS. 1–8 relate to an endoscopic diathermic knife according to a first embodiment of the present invention.

FIG. 1 is an outside view of the entire endoscopic diathermic knife.

FIG. 2 is a sectional view showing the structure of the distal end side of a sheath.

FIG. 3A is an enlarged sectional view along line A—A in FIG. 2.

FIG. 3B is an enlarged sectional view along line D—D in FIG. 4.

FIG. 4 is a sectional view along line C—C in FIG. 3A and showing the structure of the distal end side of the sheath.

FIG. 5A is a partially sectional view showing the structure of the proximal end side of the sheath.

FIG. 5B is an enlarged view of part E in FIG. 5A.

FIG. 5C is an enlarged view of part E viewed from an angle different from that in FIG. 5B.

FIG. 6 is an explanatory view of an operation for cutting a papillary sphincter via an endoscope.

FIG. 7 is an explanatory view of an operation for cutting a papillary sphincter via an endoscope by a manipulation different from that shown in FIG. 6.

FIG. 8 is an illustration showing an endoscopic image of the operation shown in FIG. 6.

FIGS. 9–12 relate to an endoscopic diathermic knife according to a second embodiment of the present invention.

FIG. 9 is a sectional view showing the structure of the distal end side of a sheath.

FIG. 10A is an enlarged sectional view along line A'—A' in FIG. 9.

FIG. 10B is an enlarged sectional view along line D'—D' in FIG. 11.

FIG. 11 is a sectional view along lines H—H and I—I in FIG. 10A and showing the structure of the distal end side of the sheath.

FIG. 12 is a perspective view of the distal end side of the sheath.

FIGS. 13–16 relate to an endoscopic diathermic knife according to a third embodiment of the present invention.

FIG. 13 is a sectional view showing the structure of the distal end side of a sheath.

FIG. 14A is an enlarged sectional view along line A"—A" in FIG. 13.

FIG. 14B is an enlarged sectional view along line D"—D" in FIG. 15.

FIG. 14C is an enlarged sectional view along line G—G in FIG. 16.

FIG. 15 is a sectional view along line H'—H' in FIG. 14A and showing the structure of the distal end side of the sheath.

FIG. 16 is a sectional view along line I'—I' in FIG. 14A and showing the structure of the distal end side of the sheath.

FIGS. 17–20 relate to an endoscopic diathermic knife according to a fourth embodiment of the present invention.

FIG. 17 is an outside view of the entire endoscopic diathermic knife.

FIG. 18 is a side view of a stone collecting basket forceps.

FIG. 19 is a sectional view showing the structure of a distal end side of a sheath with the stone collecting basket forceps received within a multipurpose lumen.

FIG. 20 is an explanatory view showing an example of stone collection by using the stone collecting basket forceps.

FIGS. 21, 22A and 22B relate to an endoscopic diathermic knife according to a fifth embodiment of the present invention.

FIG. 21 is an outside view of the entire endoscopic diathermic knife.

FIG. 22A is an illustration of a wire portion of a stone collecting basket forceps.

FIG. 22B is an illustration of an operating portion of the stone collecting basket forceps.

FIG. 23A is an illustration showing the structure of the distal end side of a sheath of an endoscopic diathermic knife according to a sixth embodiment of the present invention.

FIG. 23B is an illustration showing the structure of the distal end side of a sheath of an endoscopic diathermic knife according to a modification of the sixth embodiment of the present invention.

DETAILED DESCRIPTION OF THE PREFERRED EMBODIMENTS

Referring to FIGS. 1–8, a first embodiment of the present invention will be described.

Figure 1:
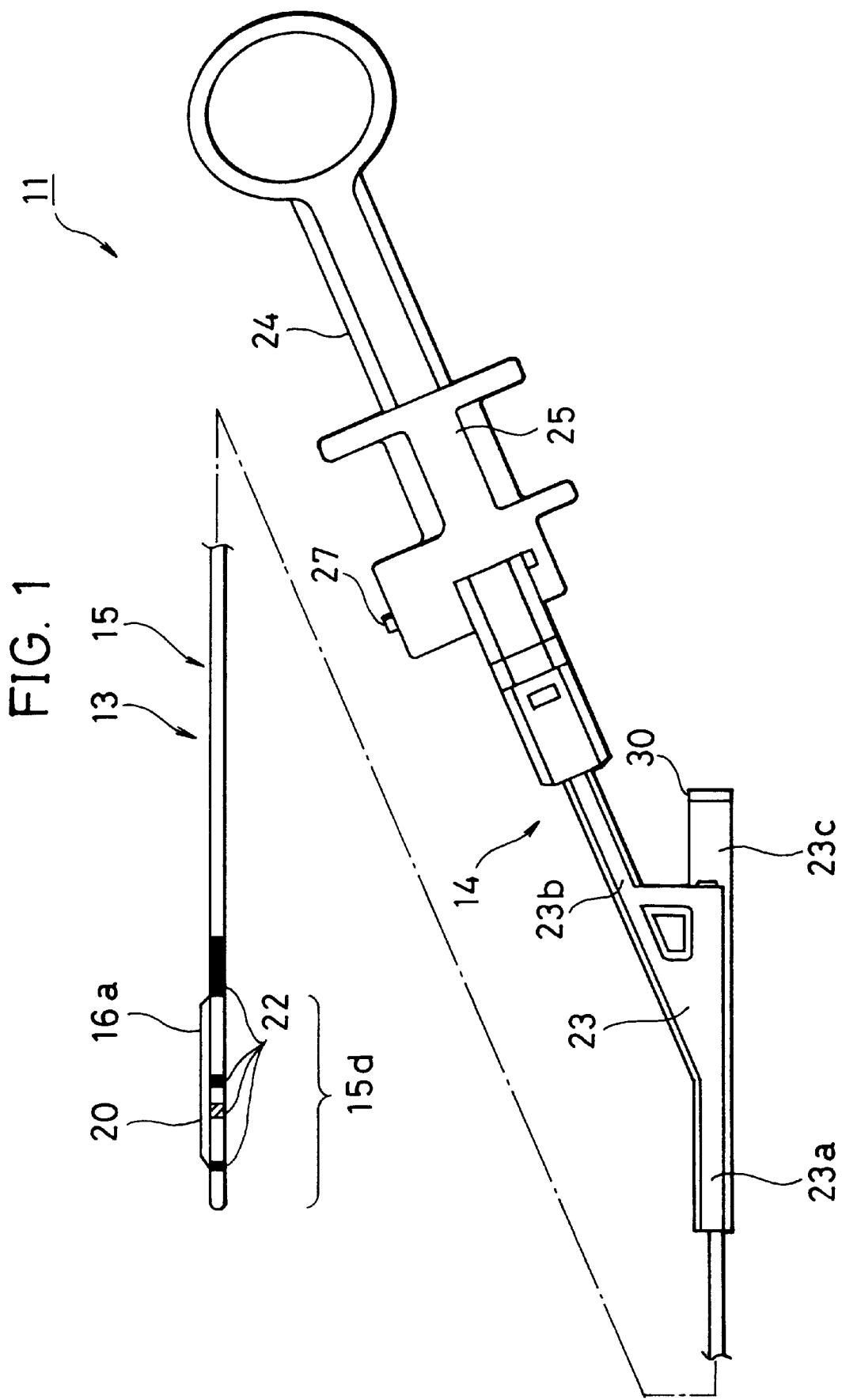

As shown in FIG. 1, an endoscopic diathermic knife (hereinafter also called merely "knife") 11 of the first embodiment of the present invention comprises a thin flexible inserting portion 13 to be inserted into a body of a patient through a treating instrument inserting channel (not shown) of an endoscope 12 (see FIGS. 6, 7 and 20); and a proximal operating portion 14 provided on the proximal end side of the inserting portion 13 so as to be operated by an operator outside the body of the patient to operate the knife 11.

As shown in FIG. 2, the inserting portion 13 of the knife 11 comprises a sheath 15 formed by an electrically insulating member. A body (sheath body) 15a of the electrically insulating sheath 15 is made of an electrically insulating thermoplastic resin, for example, a fluorocarbon resin such as PTFE and PEP. The sheath body 15a in this embodiment is formed by a flexible porous tube having three lumens.

That is, as shown in FIGS. 3A and 3B, the sheath body 15a is provided with three lumens in the axial direction (longitudinal direction) of the sheath body 15a: a wire lumen 17a for inserting an electrically conductive wire 16 such as a metal wire; a multipurpose lumen 17b having an inside diameter large enough to insert a guide wire (not shown) and/or to inject liquid (particularly contrast medium); and a reinforcing lumen 17c for inserting a reinforcing wire 18 for reinforcing the sheath body 15a.

In the wire lumen 17a in the sheath body 15a, as shown in FIG. 2, the electrically conductive wire 16 is inserted. In the multipurpose lumen 17b, the guide wire is introduced, or a liquid supplying passage is formed to inject liquid. The distal end of the multipurpose lumen 17b is open.

Further, in the reinforcing lumen 17c, a reinforcing member made of metal or the like, such as a thin but highly rigid stainless steel reinforcing wire 18, is inserted from a proximal end portion of the sheath 15 (see FIG. 5C) to the vicinity of a distal end portion 15d of the sheath 15 shown in FIG. 4. The reinforcing wire 18 is fixed in this arrangement.

A knife portion 20 is shown in dashed-double-dotted lines (also in FIGS. 11, 15 and 16) in order to clarify the positional relationship in the axial direction between the distal end of the reinforcing wire 18 and the knife portion 20.

Since the reinforcing member (i.e., the stainless steel reinforcing wire 18) is thin but highly rigid, the flexibility of the sheath body 15a can be adjusted by using the reinforcing wire 18 of a sufficiently thin outside diameter. Accordingly, there is the merit that the cross-sectional areas of the reinforcing lumen 17c and the reinforcing wire 18 in the cross section of the sheath body 15a can be sufficiently small.

Furthermore, since the stainless steel reinforcing wire 18 has a function of blocking x-rays, the position of the sheath body 15a (and thus of the reinforcing wire 18) can be confirmed under the radiation of the x-rays.

Thus, in this embodiment, the sheath body 15a is provided with the reinforcing lumen 17c and the reinforcing wire 18 is inserted therethrough to reinforce the too soft (or too flexible) sheath body 15a so as to be adequately soft.

This reinforcement makes sheath 15a adequately flexible, but not too flexible. Therefore, when the sheath 15 is inserted into a thin treating instrument inserting channel of the endoscope 12 or a living body, pushing operation on the proximal end side of the sheath body 15a can be sufficiently transmitted to the distal end portion 15d of the sheath 15, so that the sheath 15 can be easily inserted without buckling. Furthermore, since the distal end portion 15d of the sheath 15 is not reinforced, the sheath 15 is soft and can be prevented from injuring a living body when it is inserted therein. In addition, when the distal end portion 15d of the sheath 15 is bent to form the knife portion 20, the bending operation is easy.

Further, as illustrated in FIG. 2, the distal end portion 15d of the sheath body 15a is provided in its periphery with a wire lead-in opening 19a and a wire lead-out opening 19b which are communicated with the wire lumen 17a. These wire lead-in and lead-out openings 19a and 19b are provided at front and rear positions along the axial direction of the sheath body 15a.

The distal end side of the conductive wire 16 inserted into the wire lumen 17a of the sheath body 15a is led out from the sheath body 15a through the wire lead-out opening 19b and led in the sheath body 15a through the wire lead-in opening 19a so that the diathermic knife portion 20 can be formed by an exposed wire portion 16a exposed to the outside of the sheath body 15a. In this specification, as shown in FIG. 2, the portion from the distal end of the sheath 15 to the rear end of the knife portion 20 is called the distal end portion 15d of the sheath.

The conductive wire 16 is a flexible wire made of metal, such as stainless steel. The distal end of the conductive wire 16 is inserted into an X-ray blocking pipe 21 made of metal, which may comprise stainless, gold, silver, platinum, or tungsten and is fixed thereto by means of binder (such as soldering, brazing or adhesion) or welding (particularly laser welding or plasma welding).

The outside diameter of the X-ray blocking pipe 21 is set to be slightly larger than the inside diameter of the wire lumen 17a of the sheath body 15a. The X-ray blocking pipe 21 is fixed in the wire lumen 17a, on the distal end side from the wire lead-in opening 19a by means of press-fitting, adhesion, or the like.

Further, the frontmost end portion of the sheath body 15a is provided with a thin diameter portion 15b having an outside diameter D2 smaller than the outside diameter D1 (see FIG. 3A) of the intermediate portion of the sheath body 15a so as to be easily inserted.

Moreover, on the outer periphery in the vicinity of the distal end portion of the sheath body 15a, as shown in FIG. 1, a plurality of marked portions 22 are formed along the axial direction of the sheath body 15a so that the length of the sheath 15 inserted into the body can be determined approximately.

Next, the operating portion 14 of the knife 11 will be described. As shown in FIGS. 1 and 5A, the operating portion 14 is provided with a connecting member 23 which is substantially Y-shaped. The connecting member 23 is provided on its front end side with a common connecting portion 23a, and on its rear end side with branch connecting portions 23b and 23c branching into two portions. The proximal end side of the inserting portion 13 is inserted into and connected with a lumen of the common connecting portion 23a.

An operating portion body 24 is fixed to the rear end of the branch connecting portion 23b of the connecting member 23. A slider 25 is movably fitted on the operating portion body 24 so as to slide in the longitudinal direction of the operating portion body 24. The proximal end portion of the conductive wire 16 is fixed to the slider 25 via an electrically conductive operating pipe 26 (see FIG. 5B) and an electrically conductive plug 27.

The plug 27 is connected to a high frequency power unit via an electric cable (not shown). By turning on a foot switch or the like, a high frequency current flows from the high frequency power unit to the conductive wire 16, so that living tissue can be cut by the knife portion 20.

As shown in FIG. 5B, the connecting member 23 has an operating pipe lumen 28 which communicates with the wire lumen 17a of the sheath body 15a and in which the operating pipe 26 is movable back and forth. As shown in FIG. 5B, connecting member 23 also includes a branch multipurpose lumen 29 which communicates with the multipurpose lumen 17b of the sheath body 15a, as shown in FIG. 5A. The peripheral wall portion of the multipurpose lumen 17b is cut out in the vicinity of the rear end of the sheath body 15a, where the multipurpose lumen 17b communicates with the branch multipurpose lumen 29.

The operating pipe lumen 28 is provided in the branch connecting portion 23b, and the branch multipurpose lumen 29 is provided in the branch connecting portion 23c. The branch multipurpose lumen 29 is provided at its proximal end portion with a female luer mouthpiece 30 for detachably fixing an injection syringe for injecting a contrast medium or the like.

The female lure mouthpiece 30 also can be used to insert a guide wire for easily introducing the sheath body 15a to an aimed position.

FIG. 5C shows a section of part E in FIG. 5A through the reinforcing lumen 17c. In this embodiment, the reinforcing wire 18 is inserted into the reinforcing lumen 17c in the range from a proximal end portion 15c of the sheath body 15a as shown in FIG. 5C to a position just behind the distal end portion 15d of the sheath as shown in FIG. 4.

Next, the operation of the above-described endoscopic diathermic knife 11 will be described, assuming that the knife 11 is inserted into a body cavity via an endoscope 12 to cut living tissue, particularly an exit of the cavity such as a duodenal papilla 42, by high frequency current.

First, when the endoscopic diathermic knife 11 is not used, the slider 25 of the operating portion 14 is held in a stand-by position on the front end side to which the slider 25 has been moved with respect to the operating portion body 24. At this time, the distal end portion 15d of the sheath body 15a is extended in a substantially straight state.

In this state, a substantially arc-shaped bending tendency is given to the knife 20 in a range of about 15 cm from the distal end 15b of the sheath body 15a so that the knife portion 20 is oriented inward.

Figure 6:
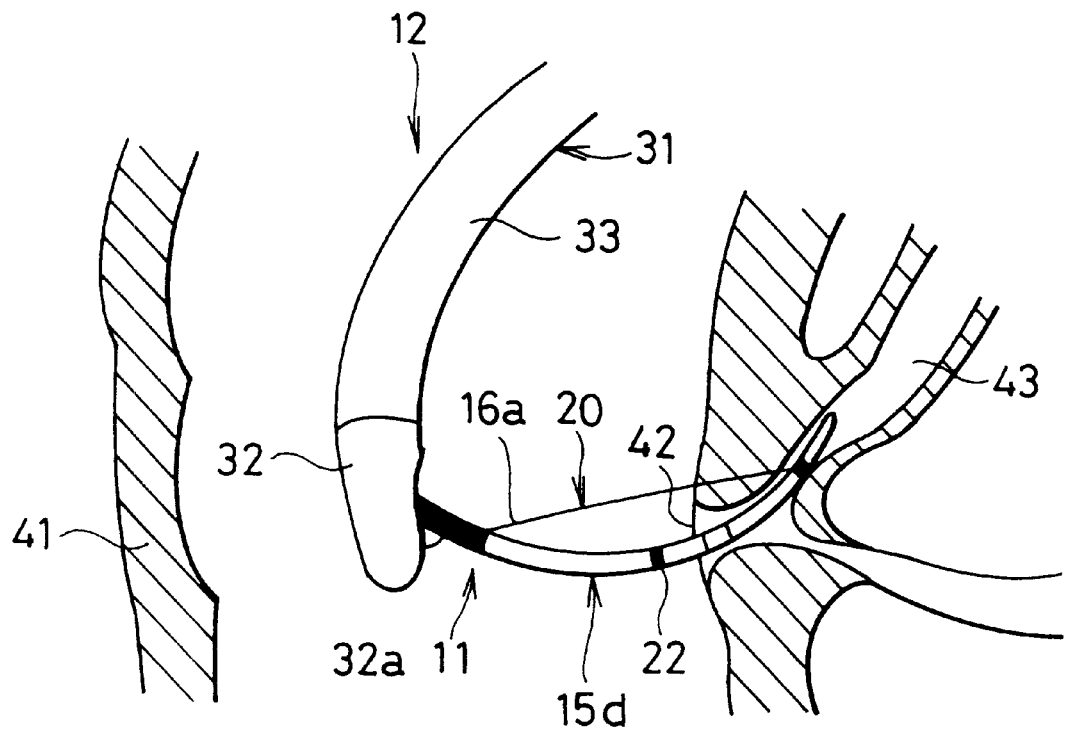

In this state, as shown in FIG. 6, the inserting portion 13 of the knife 11 is inserted into the treating instrument inserting channel (not shown) provided in an inserting portion 31 of the endoscope 12 which has been inserted into a duodenum 41 beforehand, and the inserting portion 13 of the knife 11 is protruded outward from a distal end opening of the treating instrument inserting channel provided in a distal end portion 32 of the inserting portion 31.

Figure 8:
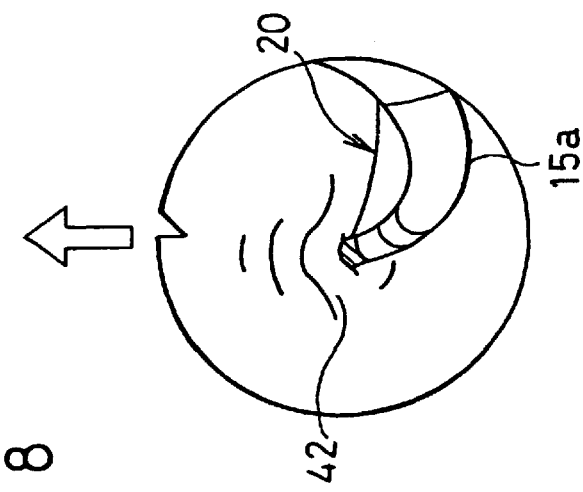
Figure 9:
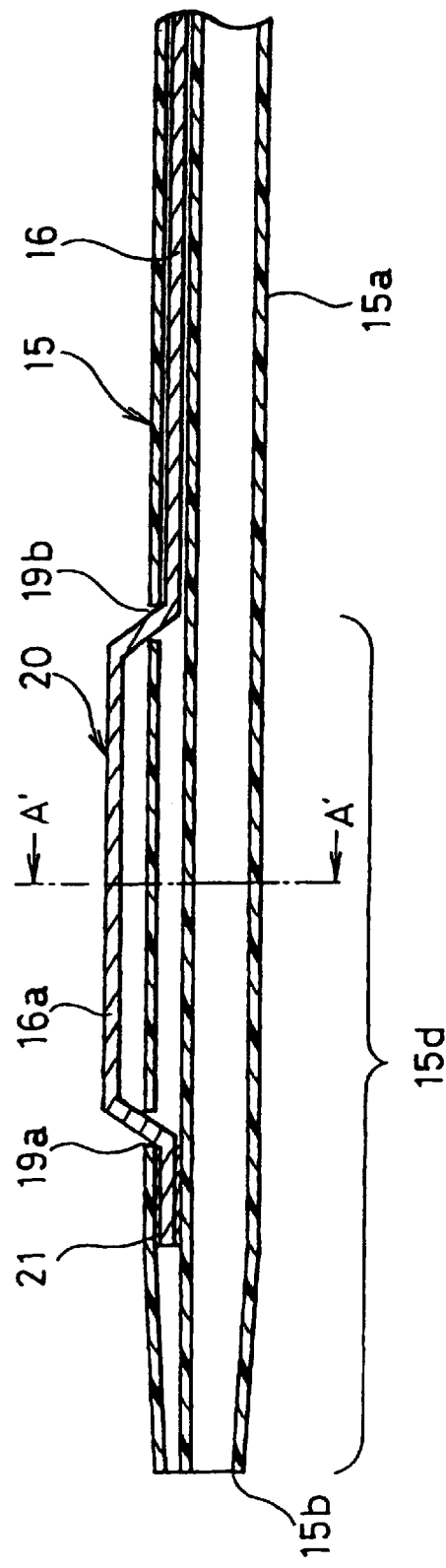

Since the substantially arc-shaped bending tendency has been given to the distal end portion 15d of the sheath beforehand, the bending tendency coincides with the bending shape of the distal end portion 32 of the inserting portion 31 and the orientation of a treating instrument upheaving device 32a so that the distal end portion 15d can be protruded with the knife portion 20 directed in the twelve o'clock direction (upward direction in the paper) in the field of view of the endoscope 12, as shown in FIG. 8.

Since the sheath body 15a is provided with the reinforcing wire 18 in its axial direction, the sheath body 15a is less flexible than that which is not provided with the reinforcing wire 18. Thus, even if the treating instrument inserting channel is small in diameter, pushing operation on the proximal end side of the sheath body 15a during its insertion can be sufficiently transmitted to the distal end portion 15d, so that the sheath body 15a can be inserted easily and quickly without buckling.

Next, the distal end portion 15d of the inserting portion 13 of the knife 11 is inserted into a bile duct 43 through a papilla 42 by a bending operation of a bending portion 33 of the inserting portion 31 of the endoscope 12, by an upheaving operation of the treating instrument upheaving device 32a provided in the distal end opening of the distal end portion 32, or by a push-pull operation of the entire inserting portion 13 of the knife 11.

Also at this time, since the sheath body 15a in the treating instrument inserting channel and the sheath portion out of the treating instrument inserting channel of the endoscope 12 are less flexible, the pushing operation on the proximal end side of the sheath body 15a is sufficiently transmitted to the distal end portion 15d of the sheath 15, so that the sheath body 15a can be easily inserted into the papilla 42 without buckling even if the papilla 42 has a small inside diameter.

Further, since the distal end portion 15d of the sheath 15 is not reinforced, the sheath 15 is soft and will not injure the vicinity of the papilla 42 and the inner wall of the bile duct 43, so that there is little danger of causing complications such as perforation and bleeding.

Subsequently, an injection syringe (not shown) is fitted in the female luer mouthpiece 30 on the branch connecting portion 23c of the connecting member 23, if necessary. Then, a contrast medium injected from the injection syringe is fed into the bile duct 43 through the branch multipurpose lumen 29 and the multipurpose lumen 17b of the sheath body 15a, thereby contrasting the inside of the bile duct 43.

Next, the depth of the insertion of the sheath body 15a into the papilla 42 is adjusted, observing as a guide the marked portions 22 on the outer periphery of the distal end portion 15d of the sheath body 15a. Also at this time, since the pushing operation on the proximal end side of the sheath body 15a is sufficiently transmitted to the distal end portion 15d of the sheath 15, the distal end portion 15d can be easily inserted.

Then, the slider 25 of the operating portion 14 is moved rearward with respect to the operating portion body 24. With this operation of the slider 25, the conductive wire 16 is pulled to the proximal end side, so that the distal end portion 15d of the sheath body 15a is bent approximately in an arc-like shape, as shown in FIG. 6. Consequently, the exposed wire portion 16a exposed to the outside of the sheath body 15a is strained like a bowstring to form the knife portion 20.

Because the distal end portion 15d of the sheath 15 is not reinforced by the reinforcing wire 18, it is soft and can be bent easily, so that good operability can be realized.

Figure 7:
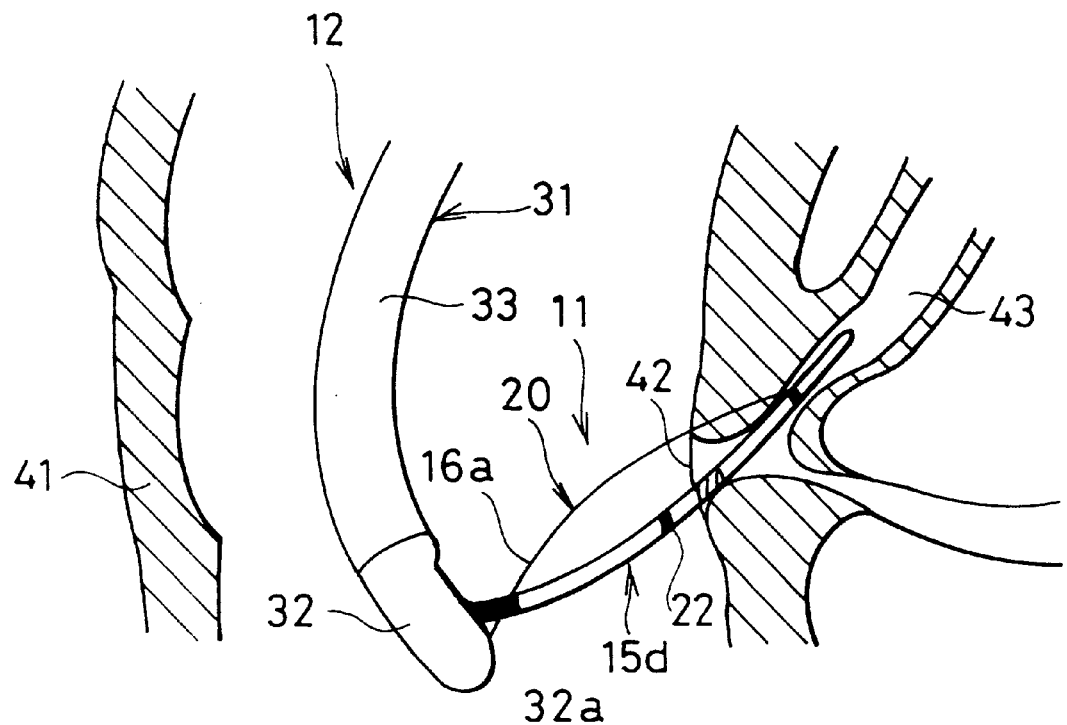

After the knife portion 20 is formed like the bowstring or a chord of a partial circle, a high frequency current is applied to the knife portion 20 to cut a papilla sphincter 42 in the upward direction in FIG. 8 (twelve o'clock direction in the field of view of the endoscope 12). After the cutting, the slider 15 is returned to its initial position and the knife 11 is drawn out of the treating instrument inserting channel of the endoscope 12. Alternatively, the slider 25 of the operating portion 14 may be moved to a direction opposite to that described above, that is, to the distal end side with respect to the operating portion body 24 so that the conductive wire 16 is pushed to form the knife portion 20 having an arc shape, as shown in FIG. 7.

This embodiment has the following effects:

According to this embodiment, because the sheath body 15a is reinforced by the reinforcing wire 18 to reduce its flexibility to an approximate level, when the sheath body 15a is inserted into the treating instrument inserting channel of the endoscope 12 and a narrow cavity, the pushing operation of the sheath body 15a on the proximal end side can be sufficiently transmitted to the distal end portion 15d, thereby improving its insertion.

Further, since the sheath 15 is reinforced in the range from its proximal end portion to the vicinity of the wire lead-out opening 19b of the distal end portion 15d without reinforcing the distal end portion 15d, the distal end portion 15d is softer than the reinforced portion and will not injure a living body when it is inserted therein. In addition, good operability can be realized because the distal end portion 15d can be easily bent.

Furthermore, this structure can be formed by only inserting the stainless steel wire into the reinforcing lumen 17c, so that the knife 11 can be assembled simply and produced at low cost. Moreover, since an X-ray blocking member such as a stainless steel wire is used as the reinforcing wire 18, the position of the sheath body 15a can be confirmed under the X-ray irradiation.

Furthermore, since the sheath body 15a is reinforced by the reinforcing wire 18 to reduce its flexibility to an approximate level, the buckling of the sheath body 15a can be effectively prevented during its insertion even if the sheath body 15a is sufficiently thin. Thus, even if the sheath body 15a has a small diameter, it can be inserted into the treating instrument inserting channel or the like to perform the cutting treatment. In this case, the knife can be used with the endoscope 12 whose treating instrument inserting channel has a small inside diameter and thus whose endoscope inserting portion 31 has a small outside diameter. Accordingly, when the endoscope 12 is inserted into a patient, the patient will have less pain. In addition, the knife 12 can be used in various body cavities, large or small.

Next, referring to FIGS. 9–12, a second embodiment of the present invention will be described.

This embodiment is different from the first embodiment in that a sheath 15 is provided with two reinforcing lumens 17c and 17d, into which reinforcing wires 18a and 18b are inserted, respectively.

As shown in FIG. 11, each of the reinforcing wires 18a and 18b is inserted from the proximal end of the sheath 15 to a position just behind a knife portion 20.

Figure 12:
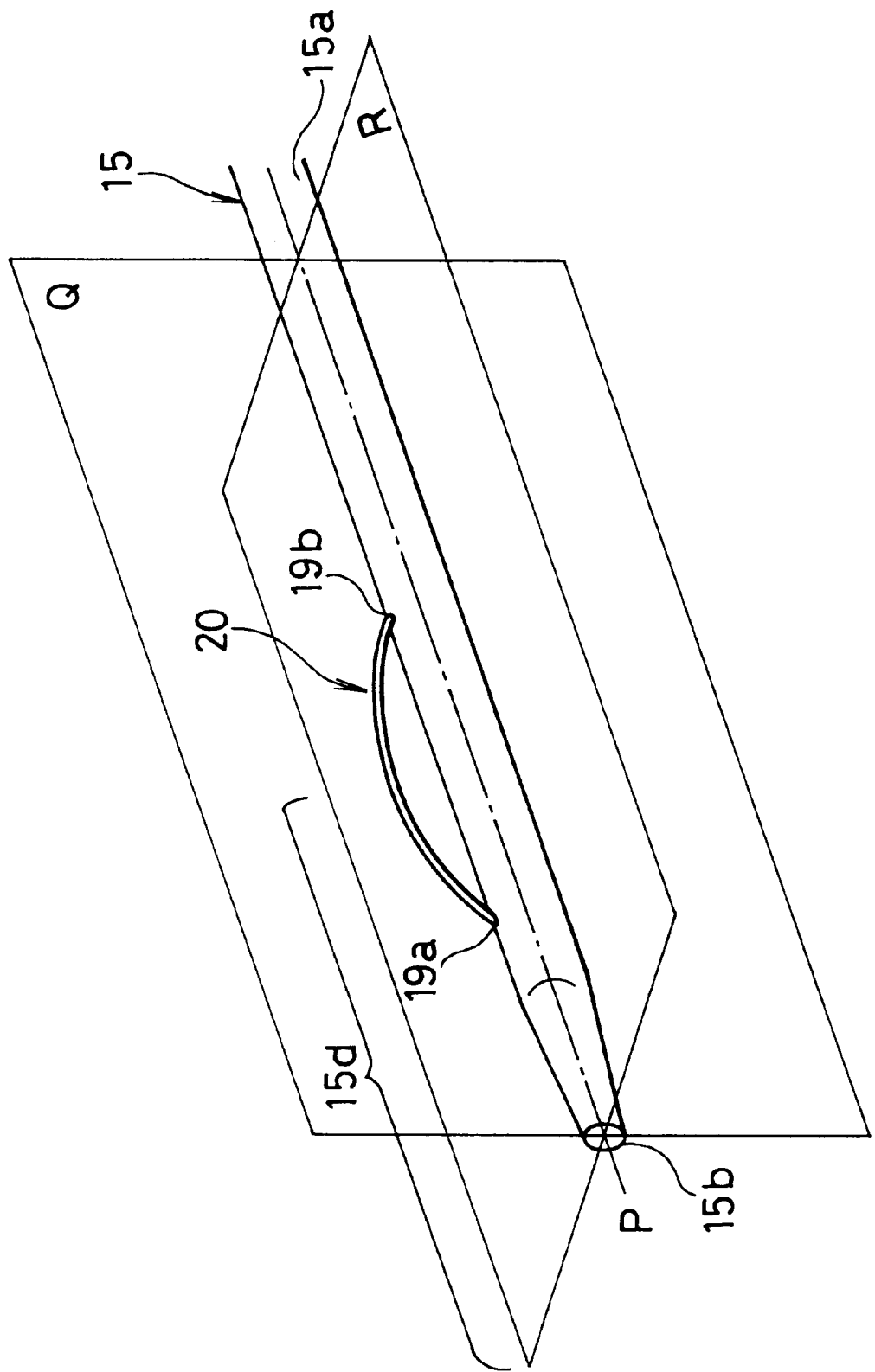

As shown in FIG. 12, the plane including the knife portion 20 and the central axis P of the sheath 15 is plane Q and the plane including the central axis P and perpendicular to plane Q is plane R. The two reinforcing wires 18a and 18b are eccentrically arranged such that the flexing resistance in plane R is larger than that in plane Q when the portion of the sheath 15 reinforced by the reinforcing wires 18a and 18b is bent.

That is, as can be seen from the sectional view of FIG. 10B also showing both planes Q and R, the two reinforcing wires 18a and 18b are eccentrically arranged in such a manner that they are close to plane R (or the distance from plane R is smaller than that from plane Q) so that the flexing resistance is larger when a sheath body 15a is bent in plane R than when it is bent in plane Q.

The operation of the present embodiment is the same as the first embodiment. First, a bending tendency of approximately an arc-like shape is given to the sheath body 15a in a range of 15 cm from its distal end of to direct the knife portion 20 inward. However, this process for giving the bending tendency may be omitted. Next, the bending tendency is further given to the distal end portion 15d by operating the slider 25 of the operating portion 14 to bend the distal end portion 15d of the sheath body 15a in an approximately arc-like shape several times.

In this state, in the same way as in the first embodiment, the sheath body 15a is inserted into the endoscope 12 and protruded out of the distal end opening of the treating instrument inserting channel.

In this case, because of the aforesaid difference of the flexing resistance of the sheath 15, the sheath 15 is not bent in plane R shown in FIG. 12, but bent in plane Q. Thus, the bending direction of the sheath 15 is regulated to coincide with the bending shape of the distal end portion 32 of the endoscope inserting portion 31 and the direction of the treating instrument upheaving device 32a, so that, as shown in FIG. 8, the knife portion 20 can be protruded in the twelve o'clock direction (upward direction in the paper) in the field of the view of the endoscope 12. Accordingly, the direction of the knife portion 20 can be maintained more accurate and stable than in the first embodiment.

This embodiment has the following effect in addition to those of the first embodiment.

Because the bending direction of the sheath 15 is regulated by arranging the two reinforcing wires 18a and 18b, it can be protruded necessarily in the twelve o'clock direction in the field of view of the endoscope 12, and the stable direction of the knife portion 20 can be realized. Accordingly, the endoscopic sphincterotomy (EST) can be performed safely without complications.

Next, referring to FIGS. 13–16, a third embodiment of the present invention will be described. FIG. 13 is a sectional view along line F'—F' in FIG. 14A and showing the structure of the distal end side of a sheath. FIGS. 14A, 14B and 14C are enlarged sectional views along line All—All in FIG. 13, line D"—D" in FIG. 15, and line G—G in FIG. 16, respectively. FIG. 15 is a sectional view along line H'—H' in FIG. 14A and showing the structure of the distal end side of the sheath. FIG. 16 is a sectional view along line I'—I' in FIG. 14A and showing the structure of the distal end side of the sheath.

This embodiment is different from the second embodiment in that the sheath 15 is provided with two reinforcing lumens 17c and 17d, in which reinforcing wires 18a and 18b with different lengths are inserted to reinforce the sheath 15.

As shown in FIG. 15, the reinforcing wire 18a is inserted in the range from the proximal end of the sheath 15 to a position which is away from the distal end face of the sheath 15 by a length of L1. On the other hand, as shown in FIG. 16, the reinforcing wire 18b is inserted in the range from the proximal end of the sheath 15 to a position which is away from the distal end face of the sheath 15 by a length of L2, where L1<L2.

The operation of the present embodiment is substantially the same as that of the second embodiment.

The present embodiment has the following effects:

Since the two reinforcing wires 18a and 18b have different lengths, the hardness of the sheath 15 can be stepwise varied. More specifically, when the sheath 15 is inserted into the treating instrument inserting channel of the endoscope 12, or the like, the proximal end side of the sheath 15 is more apt to buckle than the distal end side. Therefore, the proximal end side of the sheath 15, which is most apt to buckle, can be made to have a hardness sufficient to prevent the buckling in the axial direction of the sheath 15 by using the two reinforcing wires 18a and 18b, and the sheath portion in front of this portion can be made to have a smaller hardness sufficient to prevent the buckling by using the one reinforcing wire 18a. Finally, the distal end portion 15d of the sheath 15, which is least likely to buckle and need not be reinforced, can be flexible enough to form the knife portion 20 easily.

Further, when the sheath 15 protrudes from the treating instrument inserting channel of the endoscope 12 up to a position behind the distal end portion 15d of the sheath 15, the sheath portion in the vicinity of the exit of the treating instrument inserting channel will buckle if that portion is too soft. However, in this embodiment, since the sheath 15 is reinforced up to a position just behind the distal end portion 15d of the sheath 15 by the reinforcing wire 18a, such buckling can be prevented.

Next, referring to FIGS. 17–20, a fourth embodiment will be described.

An endoscopic diathermic knife 11, according to the present embodiment comprises a stone collecting basket forceps 51 shown in FIG. 18 combined with the endoscopic diathermic knife 11 according to the first, second and third embodiments to add to it a function of a grasping instrument for grasping a stone in a living body and excreting it to the outside of the living body.

As shown in FIG. 18, the stone collecting basket forceps 51 comprises an operating wire 52 which is provided at its distal end with a basket portion 50 as a stone grasping portion or a stone collecting portion for receiving and grasping a stone. The basket portion 50 comprises a plurality of basket wires 53 which is provided with a tendency to expand and open into a basket-like shape, and the distal ends of the basket wires 53 are bound by a distal end tip 54. Furthermore, the proximal end of the operating wire 52 is fixed to an operating pipe 55, and an operating knob 56 is fixed to the proximal end of the operating pipe 55 to form an operating portion integrally.

The basket portion 50 of the stone collecting basket forceps 51 can be inserted through a female luer mouthpiece 30 into a multipurpose lumen 17b provided in a sheath body 15a composing the knife 11'. By advancing the operating knob 56, the basket portion 50 can be set via the operating wire 52 to protrude from an opening at the distal end of the sheath 15 (the distal end opening of the multipurpose lumen 17b) of the knife 11', as shown in FIG. 17.

Figure 17:
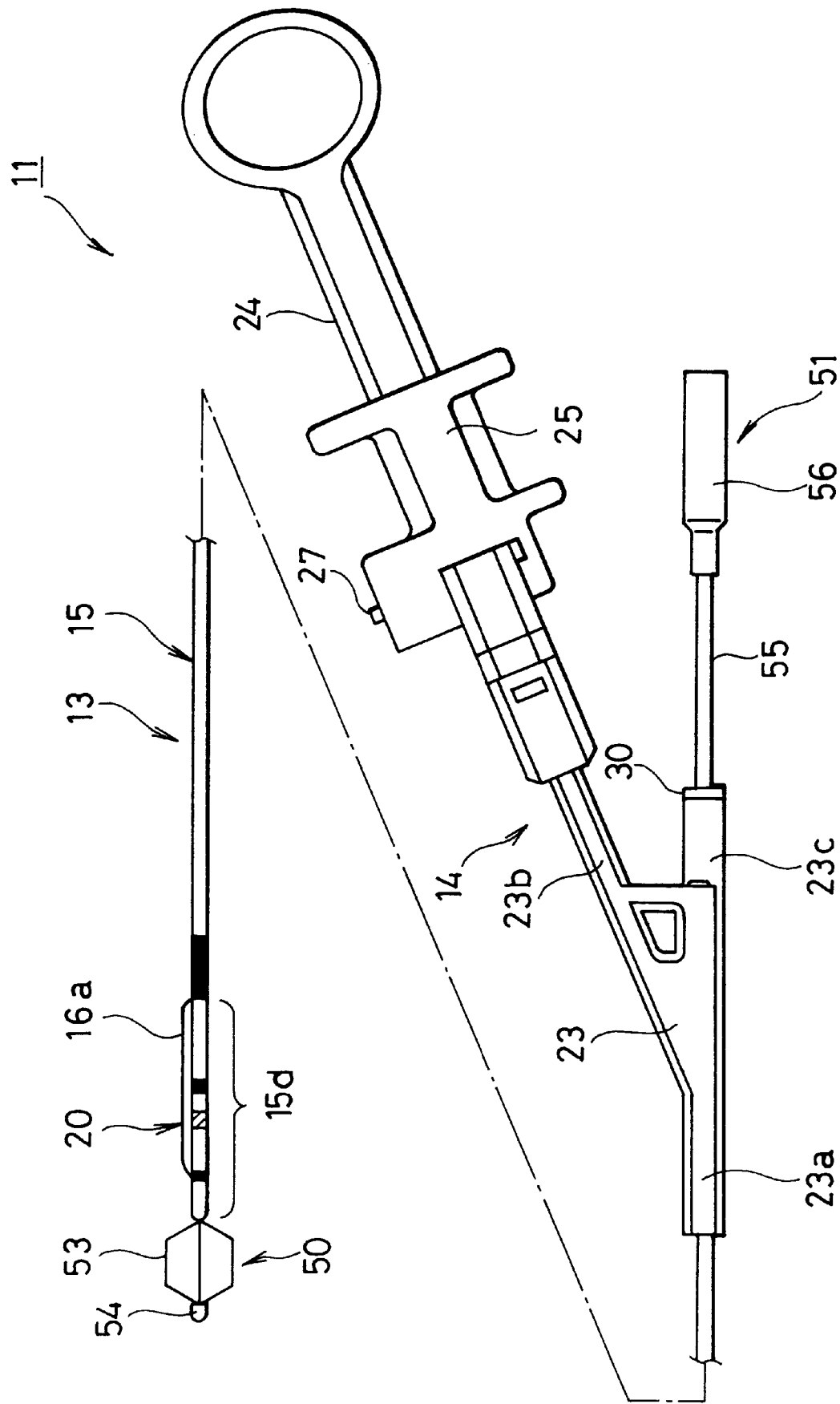

Further, by retracting the operating knob 56 in the state of FIG. 17, the basket portion 50 can be closed against its expanding and opening tendency via the operating wire 52 so as to be pulled into the multipurpose lumen 17b, as shown in FIG. 19.

Next, its operation will be described.

Figure 20:
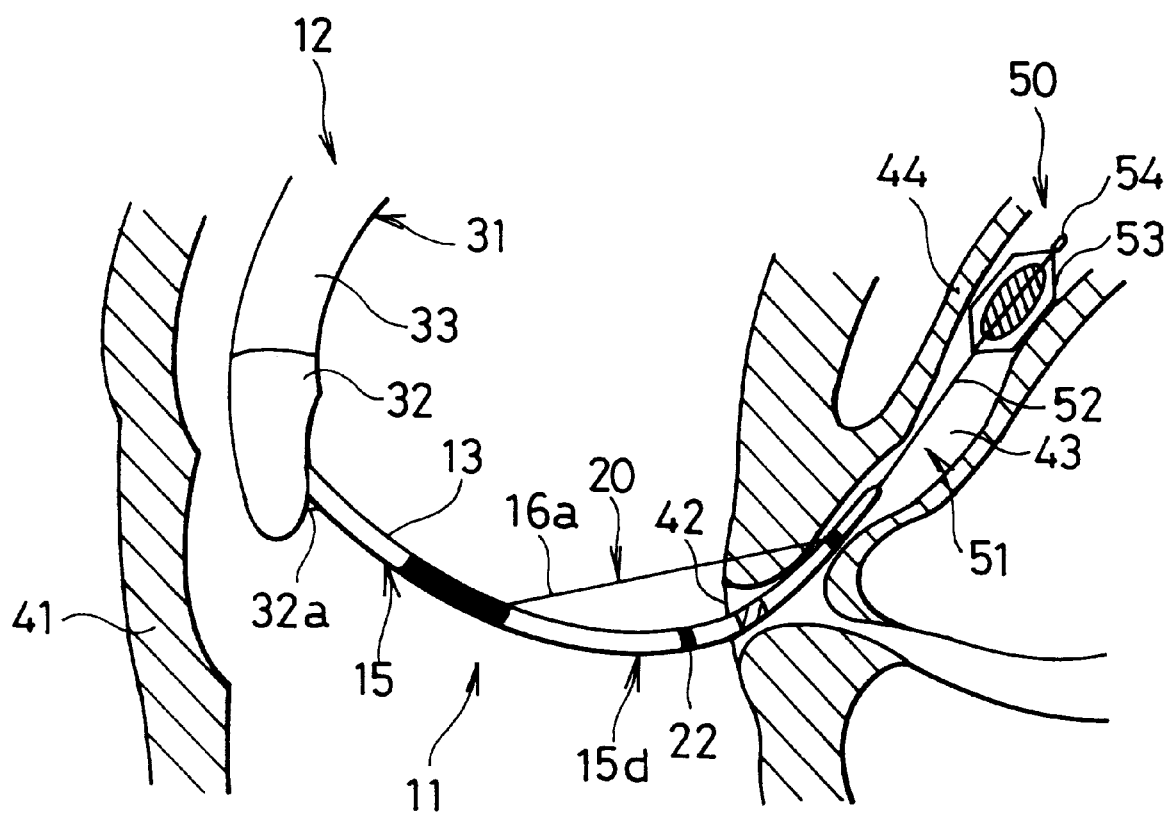

As shown in FIG. 20, if a stone 44 is formed, for example, in a bile duct 43, the endoscopic sphincterotomy (EST) is performed with the knife 11' not combined with the stone collecting basket forceps 51, that is, with the knife 11 according to the first, second and third embodiments in the same way as shown in FIG. 6.

Then, the stone collecting basket forceps 51 is inserted into the multipurpose lumen 17b of the knife 11', and the operating wire 52 is advanced to protrude the basket portion 50 out of the distal end opening of the multipurpose lumen 17b. Since the basket portion 50 is formed by the basket wires 53 given the expanding and opening tendency, it is expanded and opened into the basket-like shape. Accordingly, as shown in FIG. 20, the stone 44 is received in the expanded basket portion 50, and the operating wire 52 is further retracted to grasp the stone 44 received in the basket portion 50.

Subsequently, the sheath 15 is moved to the proximal end side to move the distal end side of the sheath 15 (the distal end portion of the sheath 15 and the basket portion 50) from the bile duct 43 into a duodenum 41, and the stone 44 received in the basket portion 50 is released from the basket portion 50 into the duodenum 41 so that the stone is naturally excreted.

The present embodiment has the following effects:

Since the endoscopic sphincterotomy and the collection of the stone 44 can be performed by one treating instrument, treatment can be made simply in a short time, and the patient will have less pain. The other effects of the present embodiment are the same as those of the first, second and third embodiments.

Figure 22A:
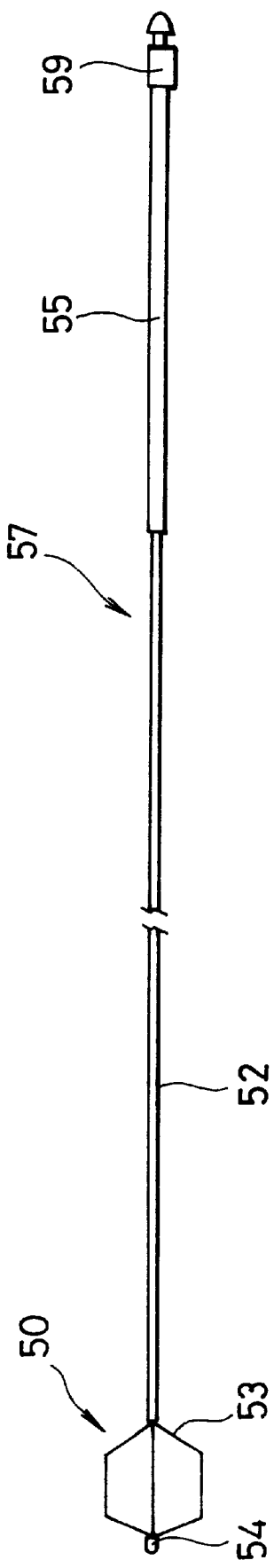
Figure 22B:
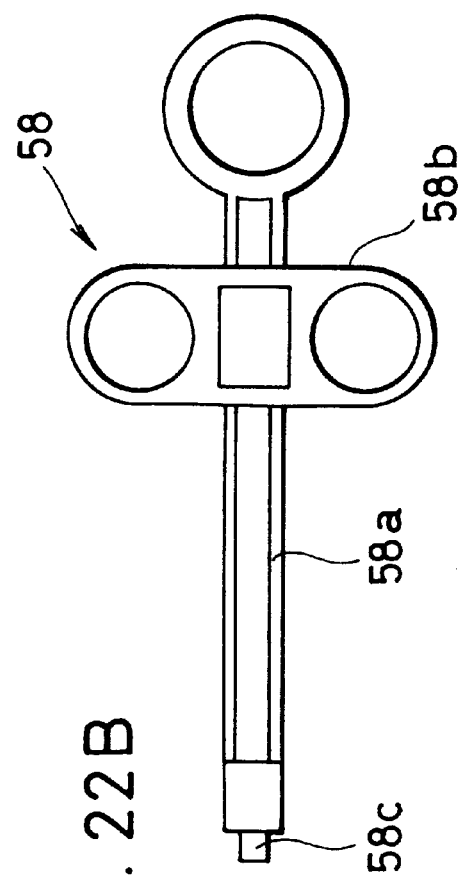

Next, referring to FIG. 21, 22A and 22B, a fifth embodiment of the present invention will be described. FIG. 21 shows an endoscopic diathermic knife of the fifth embodiment. FIG. 22A shows a wire portion of a stone collecting basket forceps. FIG. 22B shows an operating portion of the stone collecting basket forceps.

Like the fourth embodiment, an endoscope diathermic knife 11" of this embodiment as shown in FIG. 21 is such that a function of collecting a stone is added to the endoscopic diathermic knife 11 of the first, second and third embodiments. This embodiment is different from the fourth embodiment in that this stone collecting basket forceps comprises a wire portion 57 and an operating portion 58 which are detachably secured to each other, as shown in FIGS. 22A and 22B. (The stone collecting basket forceps 51 according to the fourth embodiment comprises the wire portion and the operating portion which are inseparably integrated.)

The wire portion 57 comprises an operating wire 52 which is provided at its distal end with a basket portion 50. The basket portion 50 comprises a plurality of basket wires 53, whose distal ends are bound by a distal end tip 54. An operating pipe 55 is provided at the proximal end of the operating wire 52, which is provided at its proximal end with a slider fixing portion 59.

The operating portion 58 comprises an operating portion body 58a, a slider 58b slidable thereon, and a male luer member 58c provided at the distal end of the operating portion body 58a.

The slider fixing portion 59 at the proximal end of the wire portion 57 can be fixed to the slider 58b of the operating portion 58, and the male luer member 58c at the distal end of the operating portion body 58a can be fixed to the female luer mouthpiece 30 of the endoscopic diathermic knife 11". Thus, a stone can be easily collected by grasping the operating portion 58 by a single hand to advance and retract the slider 58b.

The operation of this embodiment is substantially the same as that of the fourth embodiment.

This embodiment has the following effects:

While the knife of the fourth embodiment must be operated by both hands, the knife of this embodiment can be operated by a single hand, thereby facilitating its manipulation. This embodiment also has the same effects as those of the first, second and third embodiments.

Next, referring to FIG. 23A, a sixth embodiment of the present invention will be described. FIG. 23A shows the distal end side of a sheath 15 of an endoscopic diathermic knife according to the sixth embodiment. In this embodiment, a stone grasping portion is formed by a snare loop 60, which is different from the stone grasping portion formed by the basket portion 50 in the fourth and fifth embodiments.

The snare loop 60 comprises a pair of elastic wires 61 at the distal end of an operating wire 52, both ends of the elastic wires 61 being fixed together to form a loop-like shape, or comprises a single elastic wire 61 having a loop-like shape. A stone can be put in the snare loop 60 and grasped by receiving the proximal end side of the snare loop 60 into the multipurpose lumen 17b to squeezing the loop.

The grasped stone can be easily discharged in a duodenum 41 by protruding the snare loop 60 forward from the distal end opening of the multipurpose lumen 17b to expand.

FIG. 23B shows the distal end side of a sheath 15 in a variation of the sixth embodiment. In this variation, a stone grasping portion for grasping a stone comprises three talons 62 composed of three elastic wires 63 having an expanding and opening tendency. The distal ends of the three talons 62 are bent inward. The proximal ends of the tree wires 63 are fixed to the distal end of an operating wire 52 by brazing, soldering or the like.

The amount of expansion of the three talons 62 also can be adjusted by adjusting its amount of protrusion from the multipurpose lumen 17b, so that the stone can be grasped and released (discharged).

The sheath 15 may be reinforced by inserting the reinforcing wire 18 into the multipurpose lumen 17b without providing the reinforcing lumen 17c or the like for inserting a reinforcing member. In this case, the reinforcing wire 18 may be coated, if necessary. Further, the multipurpose lumen 17b may have a sectional shape different from a circle.

Furthermore, if a single reinforcing wire 18 is provided as in the first embodiment, the reinforcing wire need not have a circular section and may have a flat section such as a plate shape with the flat direction being perpendicular to a plane (called a "first plane") including the knife portion 20 and the central axis of the sheath 15, so that the sheath 15 can be less bent in the direction perpendicular to the first plane and easily bent in the first plane to easily perform the cutting treatment by the knife portion 20. In this case, if the conductive wire 16 is formed of a conductive material more flexible than the reinforcing wire 18, the function of the flat shape of the reinforcing wire 18 becomes relatively large and the sheath 15 is easier to bend in the first plane.

Moreover, if a sheath 15 is reinforced by the reinforcing member substantially from the vicinity of the proximal end of the sheath 15 to a position behind the wire lead-out opening and if the distal end side of the sheath has a degree of hardness which will not affect its operability and injure a living body, the present invention also covers the sheath 15 in which the reinforcing member is provided from the vicinity of the proximal end of the sheath 15 to its distal end portion. For example, the distal end side of the reinforcing member extending forward from the wire lead-out opening is made of a softer material or has a smaller cross section.

Also, an embodiment formed by partially combining the above-described embodiments falls within the scope of the present invention.

It will be obvious that widely different embodiments of the present invention may be made without departing from the spirit and scope thereof. The present invention is not limited to the preferred embodiments, except for being defined by the appended claims.

What is claimed is:

1. An endoscopic diathermic knife for use with an endoscope having a treating instrument inserting channel, the knife comprising:

an electrically insulating sheath body insertable into the treating instrument inserting channel of the endoscope and having a distal end portion, a proximal end portion, a central axis, and a plurality of lumens extending in a direction of the central axis, the plurality of lumens including at least a wire lumen and a first reinforcing lumen, the sheath body having a periphery through which a first wire opening and a second wire opening are formed in the distal end portion, the first wire opening being positioned on a side of the proximal end portion of the sheath body with respect to the second wire opening;

an electrically conductive wire inserted into the wire lumen and led out of the sheath body through the first and second wire openings to form a diathermic knife portion; and a first reinforcing member inserted into the reinforcing lumen for reinforcing the sheath body, wherein the first reinforcing member has a proximal end positioned in the proximal end portion of the sheath body, and a distal end positioned in a vicinity of the first wire opening thereof, and wherein the distal end portion of the sheath body is unreinforced by the first reinforcing member.

2. The endoscopic diathermic knife according to claim 1, wherein the plurality of lumens further includes a second reinforcing lumen and the endoscopic diathermic knife further comprises a second reinforcing member having a distal end positioned on a side of the proximal end of the sheath body with respect to the distal end of the first reinforcing member.

3. The endoscopic diathermic knife according to claim 1, wherein the first reinforcing member comprises a metallic wire.

4. The endoscopic diathermic knife according to claim 1, wherein the plurality of lumens further includes a multipurpose lumen.

5. The endoscopic diathermic knife according to claim 4, wherein the multipurpose lumen has a distal end opening, and the endoscopic diathermic knife is adapted to be used with a grasping treating instrument to be inserted through the multipurpose lumen, the grasping treating instrument having a wire portion, the wire portion having an operating wire provided at a distal end thereof with a grasping member which is to be protruded from the distal end opening of the multipurpose lumen by advancing the operating wire and which is pulled in the multipurpose lumen by retracting the operating wire.

6. The endoscopic diathermic knife according to claim 5, wherein the grasping treating instrument further includes an operating portion having an operating portion body and a slider which are movable back and forth relatively with each other, wherein the multipurpose lumen has a proximal end portion, wherein the wire portion of the grasping treating instrument has a proximal end portion, wherein the operating portion body is detachably coupled to the proximal end portion of the multipurpose lumen, and wherein the slider is detachably coupled to the proximal end portion of the wire portion of the grasping treating instrument.

7. The endoscopic diathermic knife according to claim 5, wherein the grasping member of the grasping treating instrument has an expanding tendency, wherein the grasping member is protruded from the distal end opening of the multipurpose lumen by advancing the operating wire to expand due to the expanding tendency, and wherein the grasping member is pulled in the multipurpose lumen by retracting the operating wire against the expanding tendency.

8. An endoscopic diathermic knife for use with an endoscope having a treating instrument inserting channel, the knife comprising:

an electrically insulating sheath body insertable into the treating instrument inserting channel of the endoscope and having a distal end portion, a proximal end portion, a central axis, and a plurality of lumens extending in a direction of the central axis, the plurality of lumens including at least a wire lumen and a reinforcing lumen, the sheath body having a periphery through which a first wire opening and a second wire opening are formed in the distal end portion, the first wire opening being positioned on a side of the proximal end portion of the sheath body with respect to the second wire opening;

an electrically conductive wire inserted into the wire lumen and led out of the sheath body through the first and second wire openings to form a diathermic knife portion; and a reinforcing member inserted into the reinforcing lumen for reinforcing the sheath body, wherein the reinforcing member has a proximal end positioned in the proximal end portion of the sheath body, and a distal end positioned in the vicinity of the first wire opening thereof, and wherein the reinforcing member is arranged eccentrically with respect to the central axis of the sheath body such that the sheath body has a larger flexing resistance when the sheath body is bent in a second plane instead of in a first plane, the first plane including the knife portion and the central axis of the sheath body, and the second plane including the central axis of the sheath body and being perpendicular to the first plane, and wherein the distal end portion of the sheath body is unreinforced by the reinforcing member.

9. The endoscopic diathermic knife according to claim 8, wherein the first reinforcing member comprises a metallic wire.

10. The endoscopic diathermic knife according to claim 8, wherein the plurality of lumens further includes a multipurpose lumen.

11. The endoscopic diathermic knife according to claim 10, wherein the multipurpose lumen has a distal end opening, and the endoscopic diathermic knife is adapted to be used with a grasping treating instrument to be inserted through the multipurpose lumen, the grasping treating instrument having a wire portion, the wire portion having an operating wire provided at a distal end thereof with a grasping member which is to be protruded from the distal end opening of the multipurpose lumen by advancing the operating wire and which is pulled in the multipurpose lumen by retracting the operating wire.

12. The endoscopic diathermic knife according to claim 11, wherein the grasping treating instrument further includes an operating portion having an operating portion body and a slider which are movable back and forth relatively with each other, wherein the multipurpose lumen has a proximal end portion, wherein the wire portion of the grasping treating instrument has a proximal end portion, wherein the operating portion body is detachably coupled to the proximal end portion of the multipurpose lumen, and wherein the slider is detachably coupled to the proximal end portion of the wire portion of the grasping treating instrument.

13. The endoscopic diathermic knife according to claim 11, wherein the grasping member of the grasping treating instrument has an expanding tendency, wherein the grasping member is protruded from the distal end opening of the multipurpose lumen by advancing the operating wire to expand due to the expanding tendency, and wherein the grasping member is pulled in the multipurpose lumen by retracting the operating wire against the expanding tendency.

14. An endoscopic diathermic knife for use with an endoscope having a treating instrument inserting channel, the knife comprising:

an electrically insulating sheath body insertable into the treating instrument inserting channel of the endoscope and having a distal end portion, a proximal end portion, a central axis, and a plurality of lumens extending in the direction of the central axis, the plurality of lumens including at least a wire lumen and a reinforcing lumen, the sheath body having a periphery through which a first wire opening and a second wire opening are formed in the distal end portion, the first wire opening being positioned on a side of the proximal end portion of the sheath body with respect to the second wire opening;

an electrically conductive wire inserted into the wire lumen and led out of the sheath body through the first and second wire openings to form a diathermic knife portion; and a reinforcing member inserted into the reinforcing lumen for reinforcing the sheath body, wherein the reinforcing member is provided in the range from the proximal end portion of the sheath body to the vicinity of the first wire opening such that the sheath body is reinforced substantially in the range from the proximal end portion of the sheath body to the first wire opening thereof, and wherein the distal end portion of the sheath body is unreinforced by the reinforcing member.

15. The endoscopic diathermic knife according to claim 14, wherein the plurality of lumens further includes a multipurpose lumen.

16. The endoscopic diathermic knife according to claim 15, wherein the multipurpose lumen has a distal end opening, and wherein the endoscopic diathermic knife is adapted to be used with a grasping treating instrument to be inserted through the multipurpose lumen, the grasping treating instrument having a wire portion, the wire portion having an operating wire provided at a distal end thereof with a grasping member which is to be protruded from the distal end opening of the multipurpose lumen by advancing the operating wire and which is pulled in the multipurpose lumen by retracting the operating wire.

17. The endoscopic diathermic knife according to claim 16, wherein the grasping treating instrument further includes an operating portion having an operating portion body and a slider which are movable back and forth relatively with each other, wherein the multipurpose lumen has a proximal end portion, wherein the wire portion of the grasping treating instrument has a proximal end portion, wherein the operating portion body is detachably coupled to the proximal end portion of the multipurpose lumen, and wherein the slider is detachably coupled to the proximal end portion of the wire portion of the grasping treating instrument.

18. The endoscopic diathermic knife according to claim 16, wherein the grasping member of the grasping treating instrument ha an expanding tendency, wherein the grasping member is protruded from the distal end opening of the multipurpose lumen by advancing the operating wire to expand due to the expanding tendency, and wherein the grasping member is pulled in the multipurpose lumen by retracting the operating wire against the expanding tendency.

* * * * *

UNITED STATES PATENT AND TRADEMARK OFFICE
CERTIFICATE OF CORRECTION

PATENT NO.   : 6,017,339
DATED        : January 25, 2000
INVENTOR(S)  : Sadamasa It is certified that error appears in the above-identified patent and that said Letters Patent is hereby corrected as shown below:

Title page,
Item [57], abstract, change

"The knife has the flexible, electrically insulating casing (24) inserted into a body cavity via an endoscope. A wire within this casing receives the HF current from a HF source and can be displaced to project relative to a suction opening (38) at the distal end of the casing to define the cutting zone (42).

The operating device at the proximal end of the casing has a suction mouthpiece coupling to the suction opening (38). The casing is strenghtened via an inserted support ring (56) between the suction opening (38) and the cutting zone (42) and/or via an internal strenghtening wire (50).

ADVANTAGE -- Prevents blockage of suction path during bending. (20 pp Dwg. No. 6/13)"

to

-- An endoscopic diathermic knife has a sheath insertable into a treating instrument inserting channel of an endoscope. The sheath is provided with a wire lumen for inserting an electrically conductive wire for cutting treatment, a multipurpose lumen for inserting a guide wire and/or for injecting liquid, and a reinforcing lumen for inserting a reinforcing wire that reinforces the sheath. The reinforcing wire is inserted in the range from a proximal end portion of the sheath to a position just behind a distal end portion of the sheath, so that the sheath can be easily inserted into the treating instrument inserting channel

UNITED STATES PATENT AND TRADEMARK OFFICE
CERTIFICATE OF CORRECTION

PATENT NO. : 6,017,339
DATED : January 25, 2000
INVENTOR(S) : Sadamasa

It is certified that error appears in the above-identified patent and that said Letters Patent is hereby corrected as shown below:

and the cutting treatment by a knife portion can be easy since the distal end portion of the sheath is sufficiently soft. --

Signed and Sealed this

Twenty-fifth Day of September, 2001

*Attest:*

*Attesting Officer*

NICHOLAS P. GODICI
*Acting Director of the United States Patent and Trademark Office*